United States Patent [19]

Kikuchi et al.

[11] Patent Number: 4,744,372
[45] Date of Patent: May 17, 1988

[54] HEATING APPARATUS AND METHOD FOR HYPERTHERMIA

[75] Inventors: Makoto Kikuchi, 16-19, Inokashira 1-chome, Mitaka-shi, Tokyo; Shinsaku Mori, 31-6, Okusawa 1-chome, Setagaya-ku, Tokyo; Yoshio Nikawa, 26-14, Nerima 2-chome, Nerima-ku, Tokyo; Takashige Terakawa, Tokyo, all of Japan

[73] Assignees: Tokyo Keiki Co., Ltd.; Makoto Kikuchi; Shinsaku Mori; Yoshio Nikawa, all of Tokyo, Japan

[21] Appl. No.: 757,850

[22] Filed: Jul. 22, 1985

[30] Foreign Application Priority Data

Jul. 31, 1984 [JP] Japan ................ 59-162464
Jul. 31, 1984 [JP] Japan ................ 59-162465
Jul. 31, 1984 [JP] Japan ................ 59-162466
Jul. 31, 1984 [JP] Japan ................ 59-162467

[51] Int. Cl.$^4$ ............................................. A61N 5/02
[52] U.S. Cl. .................................... 128/804; 128/400; 219/10.55 R
[58] Field of Search ............ 128/804, 399–402, 128/421–423 R; 219/10.55 R, 10.55 A, 10.55 B, 10.55 F

[56] References Cited

U.S. PATENT DOCUMENTS

| | | | |
|---|---|---|---|
| 3,077,195 | 2/1962 | Folsche | 128/804 |
| 4,108,147 | 8/1978 | Kantor | 128/804 |
| 4,140,130 | 2/1979 | Storm, III | 128/804 |
| 4,204,549 | 5/1980 | Paglione | 128/804 |
| 4,228,809 | 10/1980 | Paglione | 128/804 |
| 4,282,887 | 8/1981 | Sterzer | 128/804 |
| 4,341,227 | 7/1982 | Turner | 128/804 |
| 4,397,313 | 8/1983 | Vaguine | 128/804 |
| 4,397,314 | 8/1983 | Vaguine | 128/804 |
| 4,403,618 | 9/1983 | Turner et al. | 128/804 |
| 4,446,874 | 5/1984 | Vaguine | 128/804 |
| 4,462,412 | 7/1984 | Turner | 128/804 |
| 4,528,991 | 7/1985 | Dittmer et al. | 128/804 |
| 4,530,358 | 7/1985 | Forssmann et al. | 128/328 |
| 4,586,516 | 5/1986 | Turner | 128/804 |
| 4,589,424 | 5/1986 | Vaguine | 128/804 |
| 4,601,296 | 7/1986 | Yerushahmi | 128/804 |

FOREIGN PATENT DOCUMENTS

| | | | |
|---|---|---|---|
| 0111386 | 6/1984 | European Pat. Off. | 128/399 |
| 1440333 | 4/1969 | Fed. Rep. of Germany . | |
| 2060923 | 7/1971 | Fed. Rep. of Germany . | |
| 2648908 | 5/1978 | Fed. Rep. of Germany . | |
| 0028338 | 3/1971 | Japan . | |

OTHER PUBLICATIONS

Magin, "A Microwave System . . . Animals", IEEE Trans Microwave Theory & Tech., MTT-27, No. 1, pp. 78–83, Jan. 1979.
Robinson et al., "Techniques for Uniform . . . Carinoma", IEEE Trans Microwave Theory & Tech, MTT-26, No. 8, pp. 546–549, Aug. 1978.
"Hyperthermia in Cancer Therapy", by F. Kristian Storm, M. D., G. K. Hall Med. Pub. 1983, Title page and table of contents.
"A Localized Current Field . . . " by Astrahan et al, Med. Phys 9(3), pp. 419–424, May/Jun. 1982.
NASA Technical Brief, p. 59, Spring 1980.

Primary Examiner—Lee S. Cohen
Attorney, Agent, or Firm—Sandler & Greenblum

[57] ABSTRACT

A heating apparatus for hyperthermia utilizes electromagnetic waves for locally heating cancerous cells within a living body. Electromagnetic waves output from a single electromagnetic wave generating means are branched into a plurality of branched electromagnetic waves, which are respectively employed to conduct hyperthermia treatments for a plurality of patients. The whole of the hyperthermia system is controlled in a concentrated fashion from a single section by means of time-division multiplexing. It is therefore possible for a plurality of patients to be subjected to hyperthermia treatment at the same time and in parallel with each other, even when the conditions of these patients differ from one another. Further, it is advantageously possible to simplify the arrangement of the system as a whole and stabilize the control of the system.

10 Claims, 23 Drawing Sheets

CLOCK PULSE PERIOD

HEATING APPARATUS AND METHOD FOR HYPERTHERMIA

BACKGROUND OF THE INVENTION

1. Field of the Invention

The present invention relates to a heating apparatus for hyperthermia and, more particularly, to a heating apparatus for hyperthermia which deteriorates the regenerative functions of cancerous cells by heating them with electromagnetic waves, thereby liquidating these cancerous cells.

2. Description of the Prior Art

In recent years, hyperthermia has been given wide attention and papers have been written on hyperthermia, a therapy which deteriorates the regenerative functions of cancerous cells and thereby liquidates significant portions of them by applying heat of approximately 43° C. for one or two hours and repeating the treatment at certain intervals (MICROWAVES. October, 1976).

There are two kinds of hyperthermia therapy: general and local heating methods. Three methods have been proposed for local heating: one utilizes electromagnetic waves, the second uses electric conduction and the third uses ultrasonic waves.

Researchers have concluded that the optimum temperature for attacking cancerous cells is 43° C. or thereabouts. Temperatures below this will weaken the effects and temperatures above this will damage normal cells. Hyperthermia aims at liquidating cancerous cells without heating normal cells by maintaining the temperature in a confined narrow range.

However, it has been quite difficult when utilizing conventional means to keep the temperature of cancerous cells at approximately 43° C. for one or two hours due to the peculiar functions of a living body. In particular, heating by electromagnetic waves has been put aside for a long time because a significant portion of the electromagnetic waves is absorbed by the body surface and this method is thus unfit for heating regions deep within the body.

In view of the above-described circumstances, the inventors of this invention have previously proposed a heating apparatus for hyperthermia utilizing electromagnetic waves which is provided with function which enables accurate control of the temperature of a given heated region in a living body such that this temperature is maintained at a predetermined value over a certain period of time.

The inventors of the present invention have also previously proposed a heating apparatus for hyperthermia which is provided with a highly accurate heating control function similar to that of the apparatus proposed in the above and which enables a plurality of patients to be subjected to hyperthermia treatment at the same time and in parallel with each other.

However, the above-described apparatus (in the latter proposition) includes as one of its principal constituent elements a plurality of electromagnetic wave generating means which are respectively provided for a plurality of patients, which fact disadvantageously increases the size of the hyperthermia system as a whole and constitutes a bottleneck in relation to improvements in transportability, controllability and so forth as well as leading to an increase in costs. These problems cannot be ignored from the viewpoint of the existing necessity to increase efficiency in control of the system, to lessen the load imposed on the operator and to minimize the cost of the system for the purpose of making adequate provision of medical treatment.

Subject matter related to the present application is disclosed in the following co-pending applications, each of which is assigned to the assignee of the present invention: application Ser. No. 878,327 filed June 25, 1986; application Ser No. 878,328 filed June 25, 1986; and application Ser. No. 878,329 filed June 25, 1986; and application Ser. No. 756,071 filed July 17, 1985.

SUMMRY OF THE INVENTION

It is an object of the present invention to provide a heating apparatus for hyperthermia provided with a function which enables a highly accurate hyperthermia treatment to be applied to given regions within the bodies of a plurality of patients at the same time and in parallel with each other by utilizing electromagnetic waves and permits a reduction in the time required for the hyperthermia treatment and an increase in the efficiency of the hyperthermia treatment.

It is another object of the invention to provide a heating apparatus for hyperthermia which enables reductions in both size and cost of the apparatus as a whole and an improvement in the controllability thereof by branching the electromagnetic waves generated from a single electromagnetic wave generating means into a plurality of branched electromagnetic waves, which are respectively employed to conduct hyperthermia treatments for a plurality of patients.

It is still another object of the invention to provide a heating apparatus for hyperthermia which enables a plurality of patients to be subjected to hyperthermia treatments which are respectively appropriate for them at the same time and in parallel with each other by controlling the respective outputs of electromagnetic wave generating means respectively provided for all of the patients by time-division multiplexing such that the electromagnetic wave outputs are matched with the respective conditions of the patients, and by controlling the cooling capacity of a coolant in accordance with need.

DETAILED DESCRIPTION OF THE PREFERRED EMBODIMENTS

First Embodiment

A first embodiment of the present invention will be described hereinunder with reference to FIGS. 1 to 6.

Figure 1:
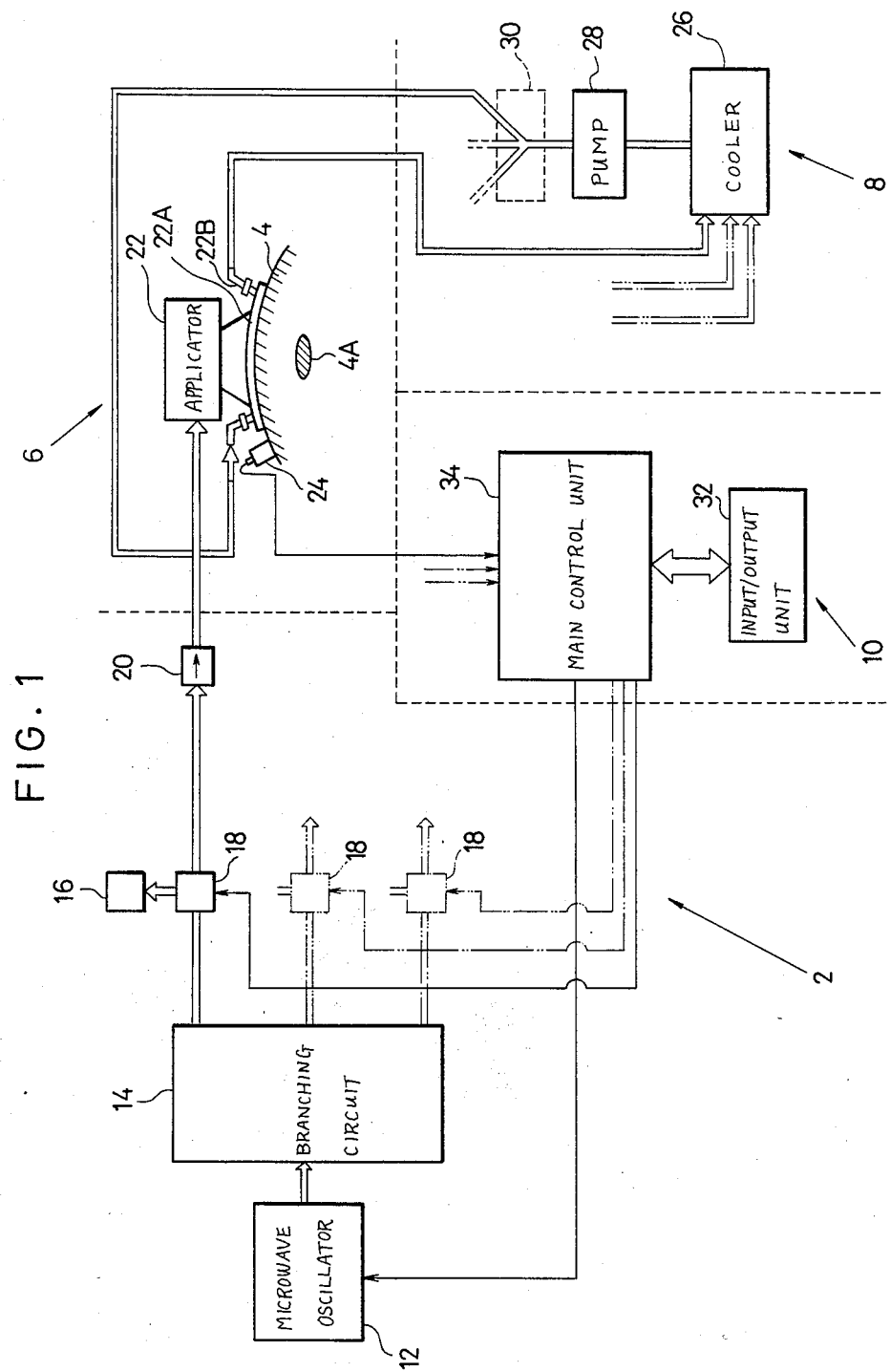
FIG. 1 is a general system diagram of a first embodiment of the present invention.

FIG. 1 is a general system diagram of the first embodiment. In this embodiment, a heating apparatus for hyperthermia includes as its principal elements an electromagnetic wave supply section 2 which generates and supplies electromagnetic waves, an electromagnetic wave irradiating section 6 which irradiates a hyperthermia treatment region (cancerous cells 4A) within the body 4 of the corresponding one of the patients with electromagnetic waves supplied from the electromagnectic wave supply section 2, a coolant supply section 8 which supplies a coolant for cooling the surface of the body 4 of each patient at the hyperthermia treatment region, and a control section 10 which performs overall control of the whole of this system.

The electromagnetic wave supply section 2 is composed of: a microwave oscillator 12 serving as an electromagnetic wave generating means which generates microwaves (e.g., 2,450 MHz); a branching circuit 4 serving as an electromagnetic wave branching means which branches the microwaves from the microwave oscillator 12 into three directions for three patients (the number of patients assumed is the same throughout the embodiments described hereinafter); coaxial switches 18 serving as electromagnetic wave switching means each of which enables the supply of the corresponding one of the microwaves branched off by the branching circuit 14 to be switched over between the corresponding electromagnetic wave irradiating section 6 and the corresponding one of the dummy loads 16; and isolators 20 each disposed on the side of the corresponding coaxial switch 18 which is closer to the corresponding electromagnetic wave irradiating section 6 and adapted to prevent any reflected wave from undesirably entering the branching circuit 14. In this case, the ratio at which electromagnetic waves are branched by the branching circuit 14 is specified in accordance with the particular structure of the branching circuit 14.

Accordingly, the microwaves supplied from the microwave oscillator 12 are branched off by the branching circuit 14 into three directions at a predetermined branching ratio (e.g., into three equal amounts). In the case where one coaxial switch 18 has been switched over to the position for supplying electromagnetic waves to the corresponding electromagnetic wave irradiating section 6, the microwaves passing through this route contribute to the hyperthermia treatment, while in the case where this coaxial switch 18 has been switched over to the corresponding dummy load 16, the microwaves are supplied to this dummy load 16, which has been matched with the actual load, and, therefore, the heating is suspended. This switching control is effected in accordance with instructions from the control section 10.

The electromagnetic wave irradiating sections 6 are disposed such as to correspond to the three systems of the branched outputs from the electromagnetic wave supply section 2. Each of the electromagnetic wave irradiating sections 6 has an applicator 22 which irradiates the body 4 of the corresponding patient with microwaves, and a cooling mechanism 22A provided on the applicator 22 and brought into contact with the surface of the body 4 to cool the body surface. Each of the cooling mechanisms 22A is recirculatingly supplied with a coolant (water is employed in this case; the same is the case with each of the embodiments described hereinafter) from the coolant supply section 8 which will be described later, whereby the body surface is cooled. In FIG. 1, the reference numeral 24 denotes an internal temperature sensor which is stuck into the cancerous cells 4A within the body 4 of each patient and adapted to detect the temperature of the cancerous cells 4A (referred to simply as the "internal temperature", hereinafter). Information thus detected is delivered to the control section 10 as illustrated.

Figure 2:
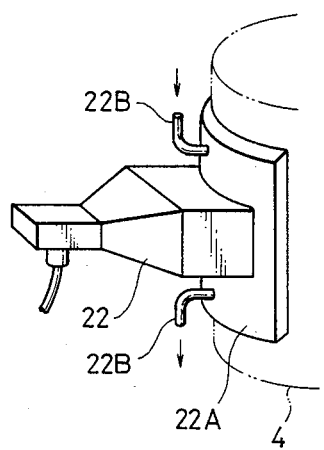
FIG. 2 is a perspective view of one example of an applicator.

One example of the applicator 22 is shown in FIG. 2. As will be clear from the Figure, the applicator 22 is an antenna which is brought into close contact with the surface of the body 4 and irradiates the body 4 with electromagnetic waves for the purpose of heating targeted cancerous cells 4A (see FIG. 1). The cooling mechanism 22A is provided in order to prevent the skin of the body from being thermally burnt which would be caused by the 4 heat generated as the result of dielectric losses in the skin at the areas of contact of the body 4 during the heating operation. For this purpose, the cooling mechanism 22A is supplied with water which is forcedly recirculated through a water circulating pipe 22B, thereby cooling the opening side of the applicator 22, that is, the body surface at the hyperthermia treatment region.

The coolant supply section 8 further includes a cooler 26 for cooling the water down to a predetermined temperature, a pump 28 for recirculating the water cooled by the cooler 26, and a coolant distributor 30 which distributes the cooled water to the respective cooling mechanisms 22A of the applicators 22.

On the other hand, the control section 10 is composed of: an input/output unit 32 to which information is input by an operator and which informs the operator of treatment conditions; and a main control unit 34 which constitutes the center of this system and both controls and manages input/output devices and the like in accordance with program and data respectively stored in program and data memory devices. The main control unit 34 is, as shown in FIG. 1, arranged such as to be fed with information detected by each of the internal temperature sensors 24 and to actuate the coaxial switches 18 and the microwave oscillator 12 in the electromagnetic wave supply section 2.

Thus, the main control unit 34 receives through an A/D (analog-to-digital) converter (not shown) the pieces of information respectively obtained by the internal temperature sensors 24 inserted into the respective bodies 4 of the three patients while successively interchanging them with each other by means of a multiplexer (not shown) provided in the main control unit 34. On the basis of the thus input information and the information which is delivered from the input/output unit 32 instructed by the operator, the main control unit 34 controls the switching operation of each of the coaxial switches 18 by outputting information via a D/A (digital-to-analog) converter (not shown) while successively interchanging each piece of output information with the others by means of a multiplexer (not shown) so that the temperature of the cancerous cells 4A (the internal temperature) within the body 4 of each patient is maintained at a desired value. In addition, the main control unit 34 delivers the various above-described information to the input/output unit 32 in order to apprise the operator of the heating conditions of each body 4. In this case, employment of the multiplexers makes it possible for a single A/D converter and a single D/A converter to process input and output information, respectively.

In the system diagram of FIG. 1, illustration of the portions of the arrangement provided for the other two patients is omitted for the purpose of simplification of the drawing (the same is the case with each of the embodiments described hereinafter).

The general operation of the above-described heating apparatus will be described hereinunder with reference to FIGS. 3 to 5. It is to be noted that, in the following description, a target value for the temperature of the body surface (referred to simply as the "surface temperature", hereinafter) which contacts the corresponding applicator 22 is set at 20° C., while a target value for the internal temperature is set at 43° C.

Figure 3:
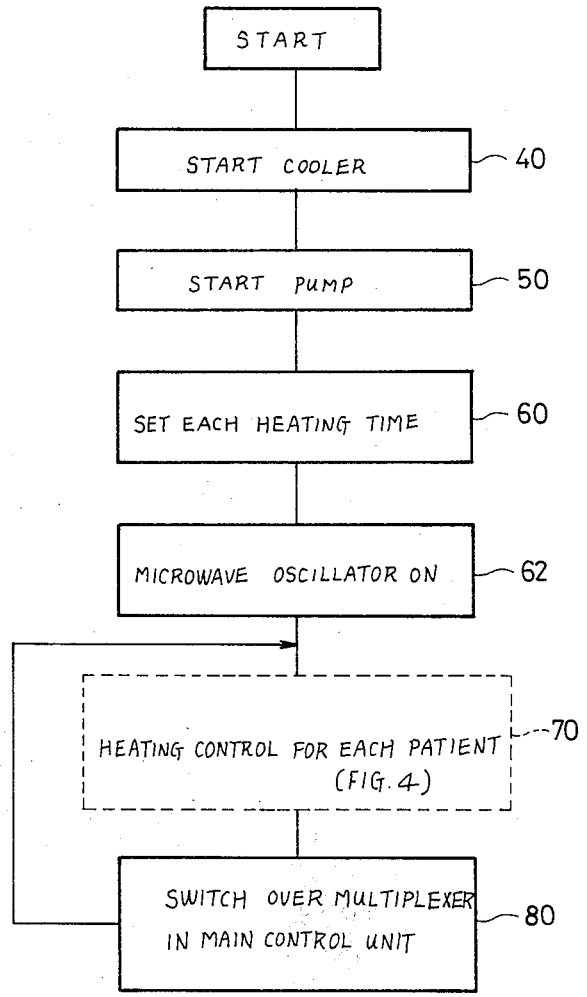
FIGS. 3 and 4 are flow charts which show the operation of the embodiment illustrated in FIG. 1.

First, the cooler 26 is started (Step 40 shown in FIG. 3), and after the water has been cooled down to 20° C., the pump 28 is started (Step 50 in FIG. 3). Then, the operator sets a heating time which is matched with the particular condition of each of the patients from the input/output unit 32 (Step 60 in FIG. 3).

After the initial values have been set as described above, the microwave oscillator 12 is turned on (Step 62 in FIG. 3), each patient is subjected to microwave irradiation (Steps 70 and 80 in FIG. 3). A detailed flow chart for this microwave irradiation is shown in FIG. 4.

Figure 4:
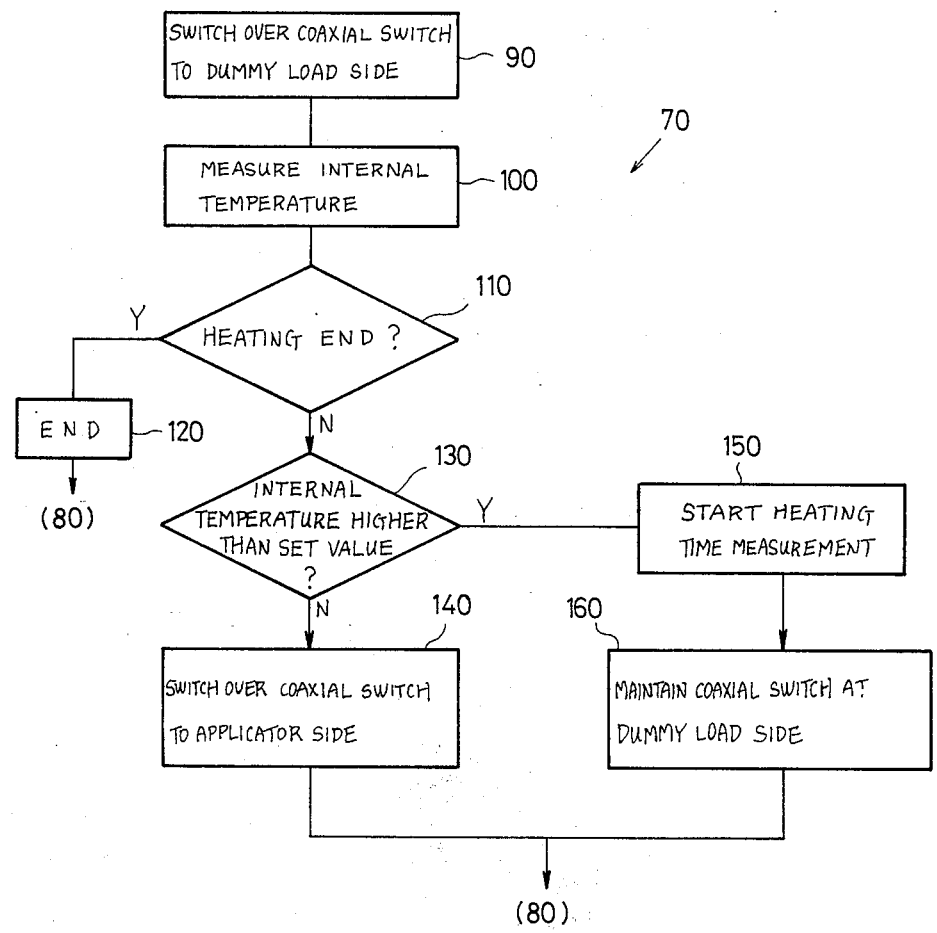

The heating control shown in FIG. 4 is executed by time-division multiplexing in synchronism with clock pulses (shown in FIG. 5) generated in the main control unit 34.

Figure 5:
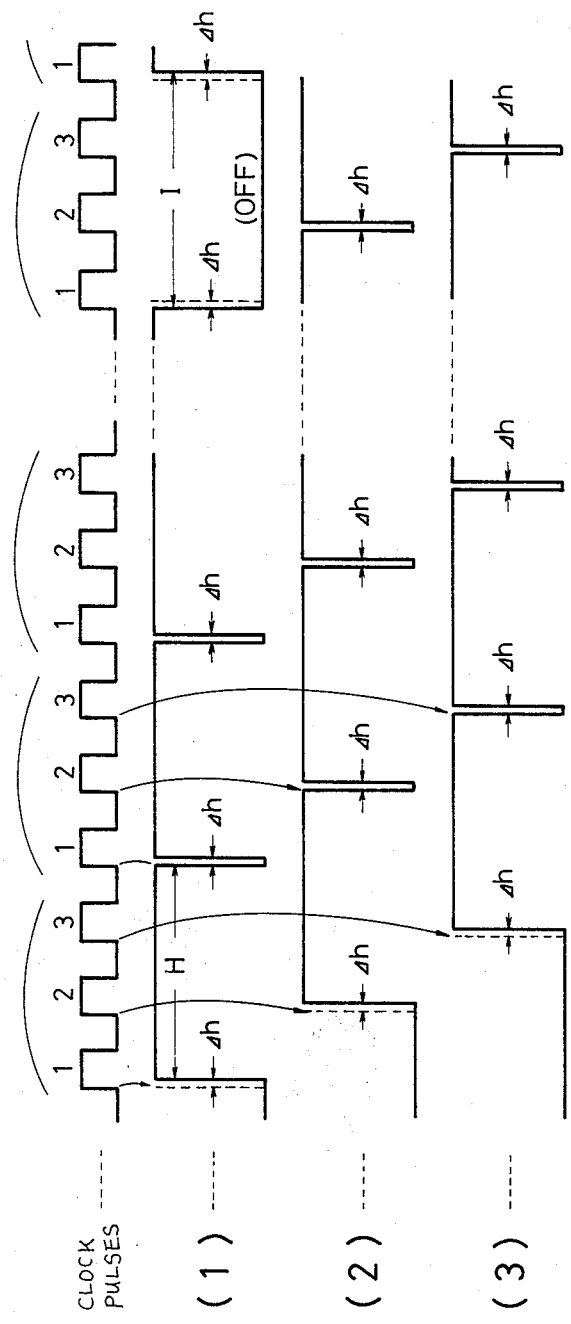
FIG. 5 is a timing chart which shows one example of the time-division multiplexing employed in the invention.

More specifically, when a clock pulse (e.g., 1) is input, the control shown in FIG. 4 is processed within a very short period of time, that is, Δ shown in FIG. 5, and the switching operation of each coaxial switch 18 for each microwave irradiation period is determined by the judgement made by the main control unit 34 which functions in response to the control shown in FIG. 4. After microwave irradiation has been effected in accordance with the control for a predetermined time (e.g., H in FIG. 5) (there are, as a matter of course, cases where the judgement made by the main control unit 34 is that no microwave irradiation is to be carried out), the processing of the control is executed again in synchronism with a subsequent clock pulse 1. Thus, treatment for a single patient is carried out through a series of processings in this way. As regards the other two patients, the heating control is processed in synchronism with clock pulses 2 and 3, respectively. Thus, it is possible for a plurality of terminal devices to be controlled by a single main control unit, and even a plurality of patients can be subjected to hyperthermia treatment at substantially the same time and in parallel with each other.

The flow chart shown in FIG. 4 will now be described in detail. When a clock pulse (e.g., 1) is input, the coaxial switch 18 for a first patient is switched over to the dummy load 16 (Step 90 in FIG. 4) in order to measure the internal temperature of this patient. Thus, after the microwave irradiation has been suspended so that the body 4 is not irradiated with microwaves, the internal temperature is measured (Step 100 in FIG. 4). The reason why no microwave irradiation is carried out during the measurement of internal temperature is that if microwave irradiation is continued, the internal temperature sensor 24 inserted into the body 4 of the patient would be affected by the microwave, which fact would lead to errors in measurement of the internal temperature. After the internal temperature has been measured, a judgement is made (Step 110 in FIG. 4) as to whether or not the heating time has reached the value previously set (see Step 60 in FIG. 3). If YES, the treatment for the first patient alone is ended, and the process shifts to steps for treating another patient (Step 120 in FIG. 4; Step 80 in FIG. 3). More specifically, the multiplexers in the main control unit 34 are switched over, and input output ports (not shown) of the main control unit 34 are changed over to the internal temperature sensor 24 and the coaxial switch 18 for the second patient (Step 80 in FIG. 3), thus executing processing for the second patient in a manner similar to the above.

If the judgement (Step 110 in FIG. 4) indicates that the heating time has not yet reached the set value, a judgement is made (Step 130 in FIG. 4) as to whether or not the internal temperature (the temperature of cancerous cells) measured beforehand is higher than a set value (43° C.) which has previously been input by the operator. When the internal temperature is lower than the set value, the main control unit 34 gives instructions to the coaxial switch 18 concerned whereby it is switched over to the corresponding applicator 22 (Step 140 in FIG. 4) (while the microwave oscillator 12 is kept ON), and heating for hyperthermia is continued until a subsequent pulse 1 occurs. More specifically, the microwave irradiation and measurement of internal temperature are repeated until the internal temperature becomes higher than the set value.

On the other hand, when the judgement (Step 130 in FIG. 4) indicates that the internal temperature becomes higher than the set value as a result of the above-described microwave irradiation, measurement of the heating time is immediately started by the main control unit 34 (Step 150 in FIG. 4). At this time, since the internal temperature (the temperature of cancerous cells) is slightly higher than the set value, the switching of the coaxial switch 18 to the dummy load 16 is maintained as it is (Step 160 in FIG. 4) for the purpose of lowering the internal temperature, so that no microwave irradiation is effected. If the internal temperature is lower than the set value when a subsequent clock pulse 1 occurs, microwave irradiation is effected again in the above-described Step 140. This repetition of the heating control is effected within a very short period of time by the above-described time-division multiplexing, whereby a highly accurate heating for hyperthermia is continued over a long period of time for each of the patients, as shown in FIG. 6 which will be described later.

In this case, the main control unit 34 is programmed such that, when repeating the heating control shown in FIG. 4, the main control unit 34 actually executes only those steps which need to be executed for each repetition of the heating control. For example, a program is arranged such that, if Step 150 in FIG. 4 "Start Heating Time Measurement" is once executed, this Step 150 is skipped in the control effected thereafter. In addition, when treatment for all the patients has been completed, a display lamp (not shown) is turned on, and the drive of the apparatus is suspended by the operator.

Figure 6:
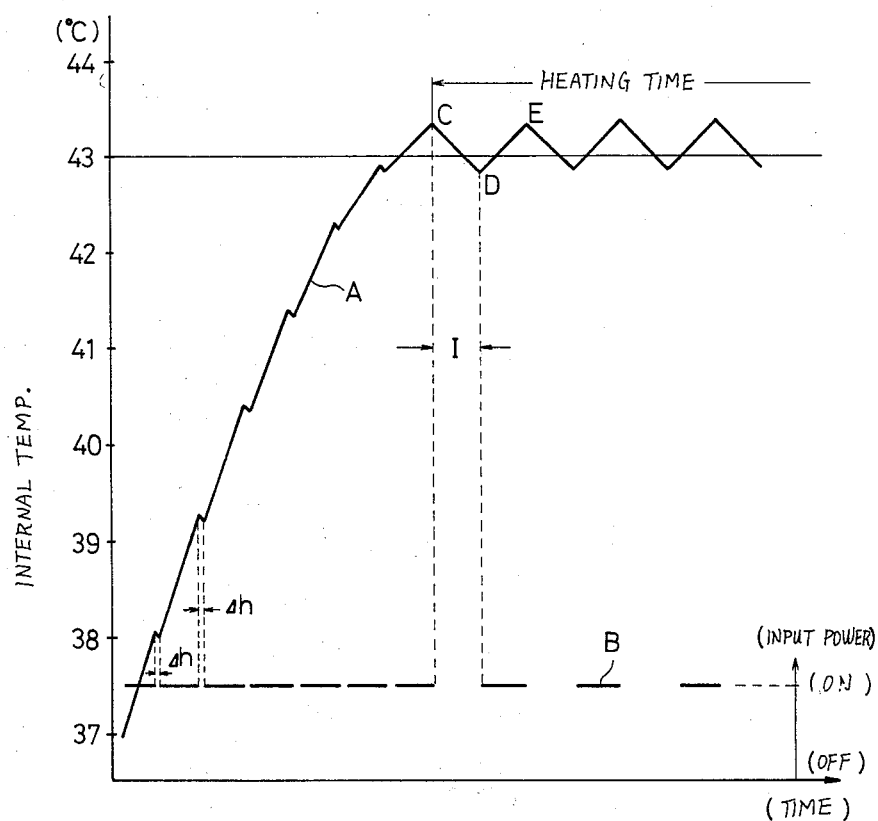
FIG. 6 is a graph which shows the action and operation of the embodiment illustrated in FIG. 1.

FIG. 6 shows a curve A representing changes with time in the internal temperature (the temperatures of cancerous cells) of a single patient measured during each microwave irradiation period, each non-irradiation period and each internal temperature measuring period (during which the heating control shown in FIG. 4 is processed), together with a broken line B representing changes in the microwave output.

In FIG. 6, each of the intervals in which the internal temperature curve ascends corresponds to a microwave irradiation period, while each of the intervals Δ in which the temperature curve descends corresponds to a period during which an internal temperature measuring operation is effected in synchronism with one clock pulse, as shown in FIG. 5. During each of the internal temperature measuring periods, the microwave output to the applicator 22 is zero (see Step 90 in FIG. 4). The point C in FIG. 6 represents a point of time at which the internal temperature first exceeds the set temperature as the result of the microwave irradiation and the measurement of the heating time is hence started. The above-described heating time is counted from this point C. The length of the period of time after the internal temperature has reached 43° C. or thereabouts is one of the primary factors used in reaching a decision as to whether or not it is possible to liquidate cancerous cells. For this reason, the heating time is set in accordance with the particular condition of each patient (Step 60 in FIG. 3) as described above.

Thereafter, instructions are continuously given to the coaxial switch 18 to switch it over to the dummy load 16 during each internal temperature measuring period until the internal temperature reaches 43° C. or below (in Step 160 in FIG. 4; see the period between C and D in FIG. 6), and at the point of time when the internal temperature reaches 43° C. or below, microwave irradiation is resumed (during the period between D and E in FIG. 6). The time I between C and D corresponds to the time I, for example, which is shown in FIG. 5. By virtue of such repetition of control, it is possible for the internal temperature of each patient to be maintained at the set value or at values in close proximity thereto over a long period of time. Since an internal temperature above 45° C. adversely affects normal cells, it is necessary for the microwave output and the irradiation period to be set such that the internal temperature does not exceed 45° C. at any time during the heating treatment.

As has been described above, it is possible according to the first embodiment to effect a highly accurate control such that the internal temperature is maintained at a set value or at values in close proximity thereto over a long period of time, and it is possible for even a plurality of patients to be subjected to hyperthermia treatment at the same time and in parallel with each other, which fact advantageously leads to a further increase in treatment efficiency. Since in this case a single microwave source (microwave oscillator) and a single main control unit are conveniently used in common to control the various terminal devices, it is favorably possible to reduce the size of the apparatus as a whole, improve its transportability and controllability and hence lessen the load imposed on the operator in contrast to a hyperthermia apparatus which is equipped with a plurality of electromagnetic wave generating means. Further, in this embodiment the electromagnetic wave generating means is continuously kept operative and, while doing so, microwaves generated thereby are effectively ON/OFF controlled by the electromagnetic wave switching means, which fact advantageously facilitates the control operation. Moreover, when a plurality of patients are simultaneously subjected to hyperthermia treatment, control is effectively executed for each individual patient. It is therefore advantageously possible for various patients to be individually subjected to treatments in parallel with each other which are individually suitable to them even when the conditions of these patients differ from one another by properly setting respective heating times.

It is to be noted that the first embodiment exemplifies the arrangement which incorporates the main control unit 34, the internal temperature sensors 24 serving as heated region temperature detecting means, the coaxial switches 18 serving as electromagnetic wave switching means and so forth, and particularly discloses a technical means in which the switching operation of each of the coaxial switches 18 is automatically controlled by means of the main control unit 34. However, the most fundamental object of enabling a plurality of patients to be simultaneously subjected to hyperthermia treatment can be sufficiently accomplished simply by employing such an arrangement that the branching circuit 14 is provided between the microwave oscillator 12 and the applicators 22, and the applicators 22 are individually connected to a plurality of output terminals of the branching circuit 14. As regards superficial cancers, for example, skin cancer, it is possible to effect treatment, according to the type of cancer, in such a manner that the operator directly handles an applicator on the surface of the body of the patient and asks him the extent of heat. In such a case, it is unnecessary to specially employ the main control unit 34.

In the above-described modification, when two patients are subjected to hyperthermia treatment by employing an apparatus which includes a branching circuit 14 having, for example, three output terminals, coaxial switches 18 are respectively connected to the output terminals in a manner similar to that in the above-described embodiment such that it is possible for any one of the output terminals to be selectively cut off as desired, and the coaxial switches 18 are respectively provided with dummy loads which effectively absorb the electromagnetic waves which are supplied thereto by the respective switching operations of the coaxial switches 18. In such an arrangement, the switching over of the coaxial switches 18 is manually effected by the operator for each applicator 22 in accordance with need, whereby it becomes unnecessary to specially employ the main control unit 34 and the internal temperature sensors 24 of the first embodiment, which fact advantageously permits remarkable simplification of the apparatus as a whole and reduces the cost thereof.

Further, in the above-described modification, when no coaxial switch 18 is employed as an electromagnetic wave switching means, it is also possible to adopt an arrangement wherein the dummy loads 16 are directly and detachably mounted on the respective applicators 22, and the operator handles each dummy load 16 for each individual applicator 22 in accordance with need. In such a case, it is advantageously possible to simplify the apparatus as a whole and ensure the safety of the body of a patient since there is no fear of the body being undesirably heated by any applicator which should be inoperative.

Second Embodiment

A second embodiment of the invention will now be described with reference to FIGS. 7 to 9, in which the same constituent elements as those in the first embodiment are denoted by the same reference numerals (the same is the case with each of the embodiments described hereinafter).

The second embodiment aims at facilitating and expenditing the control of internal temperature by individually controlling the cooling of the surface of the body of each patient during hyperthermia treatment so that the surface temperature is properly adjusted, in addition to the object of the above-described first embodiment. To this end, the flow rate of cooling water in the second embodiment is controlled.

Figure 7:
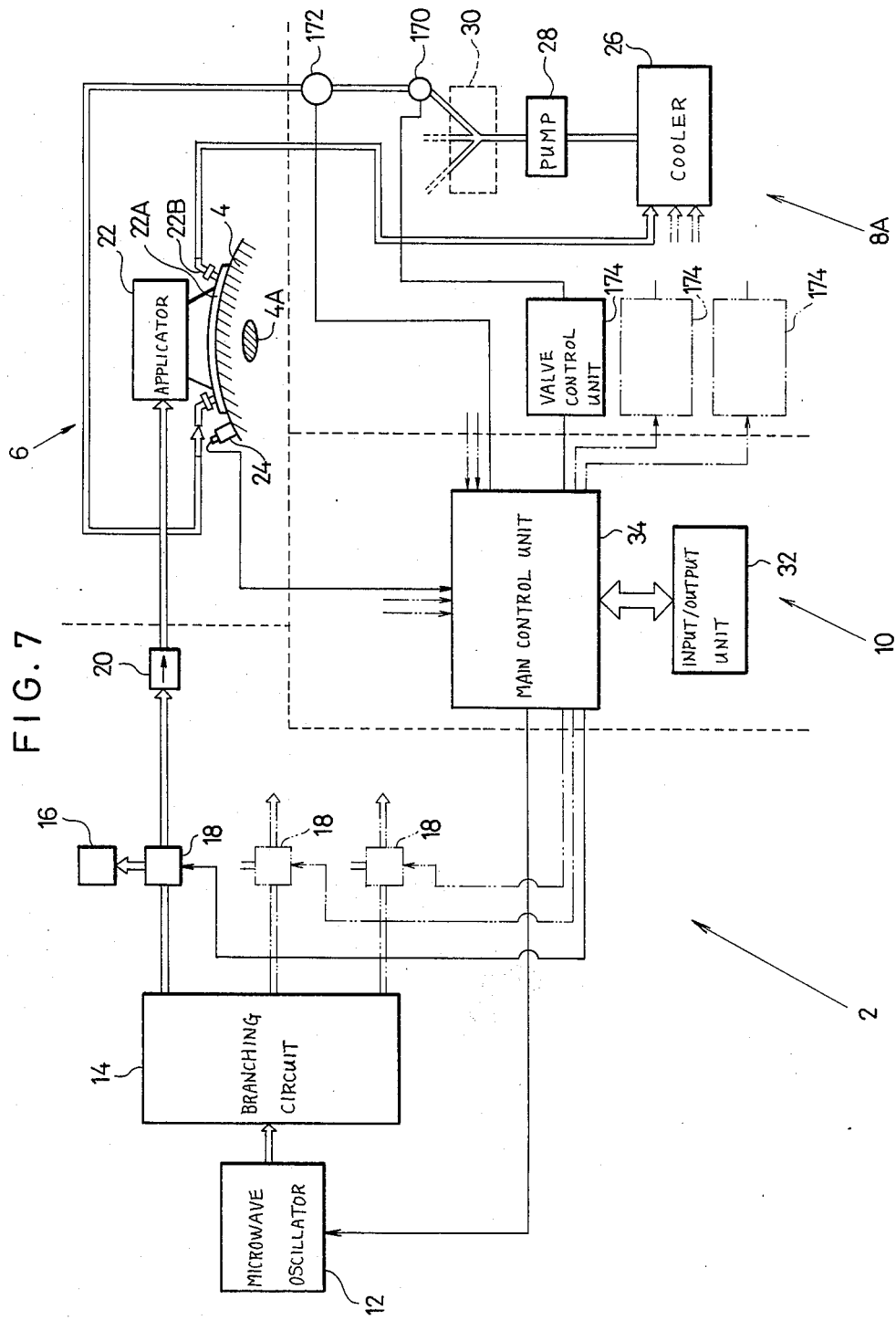
FIG. 7 is a general system diagram of a second embodiment of the invention.

Referring first to FIG. 7, in the cooling water supply section 8A of this embodiment, water is distributed by the coolant distributor 30 to the respective cooling mechanisms 22A. The coolant distributor 30 is provided on its outlet side with flow rate adjusting valves 170 and flow rate sensors 172, which correspond to the respective cooling mechanisms 22A. The flow rate information detected by each of the flow rate sensors 172 is input to the main control unit 34 in the control section 10 and is subjected to a judgement by a predetermined control function of the main control unit 34. The main control unit 34 delivers control signals to valve control units 174 respectively provided for the valves 170 in accordance with need, thereby controlling the degree of opening of the corresponding valves 170. In consequence, the flow rate of cooling water is adjusted in accordance with the degree of opening of each valve 170, and the temperature of the body surface at the hyperthermia treatment region is thereby adjusted. This adjustment of the temperature of the body surface is an auxiliary means relative to the internal temperature control. In this case, inputting of flow rate information to the main control unit 34 and delivering of control signals from the main control unit 34 are effected for each of the systems by the switching operation of the multiplexers in a manner similar to that in the first embodiment. Each of the internal temperature sensors 24 functions as a heated region temperature detecting means.

The arrangement of the other portions of the second embodiment is the same as that of the first embodiment.

The following is a description of the general operation of the second embodiment with reference to FIGS. 8 and 9, in which those steps which represent the same operations as the ones in the first embodiment are denoted by the same reference numerals (the same is the case with each of the embodiments described hereinafter). A setting value for the internal temperature is assumed to be 43° C.

Figure 8:
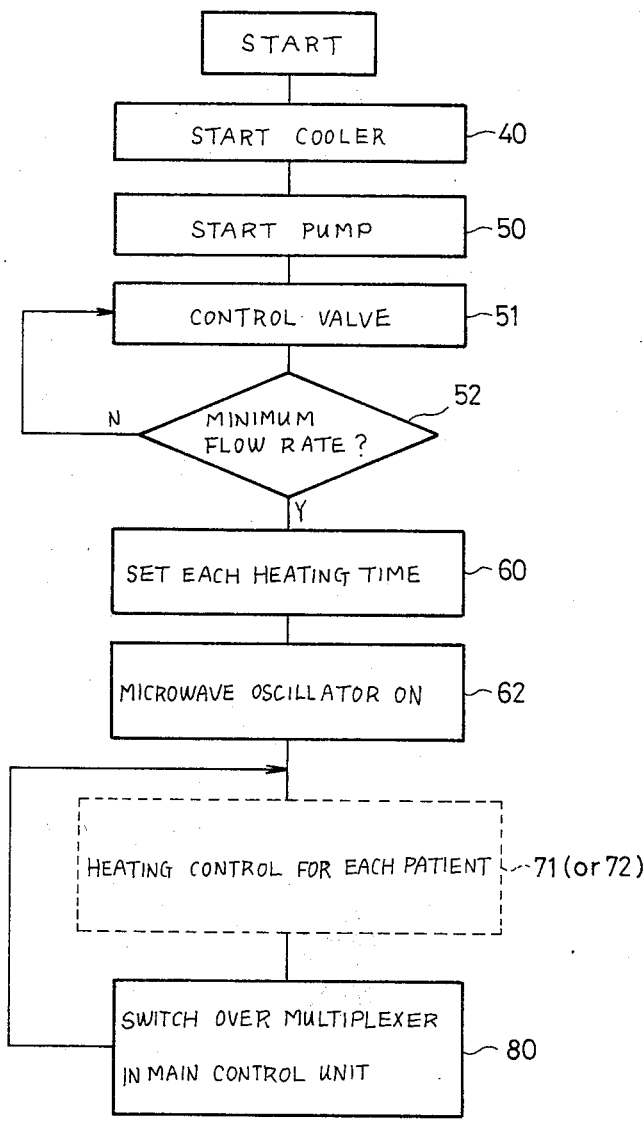
FIG. 8 is a flow chart which shows the operation of the embodiments respectively illustrated in FIGS. 7 and 10.

First, the cooler 26 is started (Step 40 in FIG. 8), and the pump 28 is started (Step 50 in FIG. 8). Then, the degree of opening of each valve 170 is controlled on the basis of the flow rate information obtained by the corresponding flow rate sensor 172 such that the amount of cooling water recirculating is minimized (Step 51 and 52 in FIG. 8). Then, in a manner similar to that in the first embodiment, a heating time for each patient is set (Step 60 in FIG. 8), and the microwave oscillator 12 is turned ON (Step 62 in FIG. 8). Thereafter, a heating control peculiar to each patient is individually effected by time-division multiplexing until the treatment for all the patients is ended (Steps 71 and 80 in FIG. 8). This time-division multiplexing is of a form which is the same as that in the first embodiment (see FIG. 5). (The same is the case with each of the embodiments described hereinafter).

Figure 9:
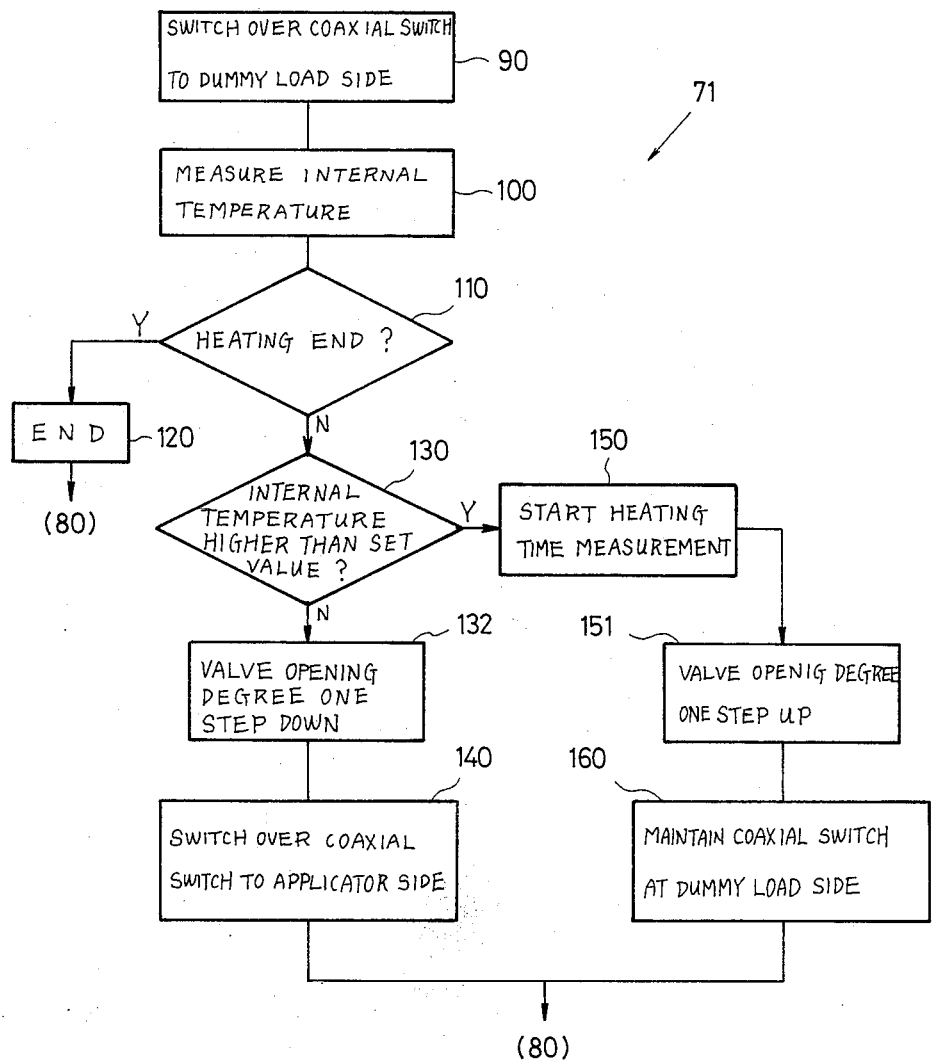
FIG. 9 is a flow chart which shows the operation of the embodiment illustrated in FIG. 7.

The heating control for each individual patient is effected in accordance with the flow chart shown in FIG. 9. According to this flow chart, the following control process is added to the control operation of the first embodiment. Namely, in accordance with the result of the judgement (Step 130 in FIG. 9) as to whether or not the internal temperature is higher than the set value, the corresponding valve 170 is closed (Step 132 in FIG. 9) or opened (Step 151 in FIG. 9) by one step. The other operations of this embodiment are the same as those shown in FIG. 4 which illustrates the operation of the first embodiment.

In the above-described control, when the internal temperature is lower than the set value, the valve 170 is closed by one step (Step 132 in FIG. 9). This is done because it is necessary to raise the surface temperature (however, in this case it is necessary for the flow rate of cooling water to be high enough to maintain a minimum amount of cooling water for recirculation in order to prevent the surface of the body of the patient from being thermally burned) and thereby to effect an auxiliary temperature adjustment also at the surface of the patient body so that the temperature of cancerous cells (the internal temperature) being heated by the microwave irradiation quickly reaches the set value. Thereafter, the coaxial switch 18 is switched over to the applicator 22, whereby heating is effected (Step 140 in FIG. 9). On the other hand, the reason why the valve 170 is opened by one step (Step 151 in FIG. 9) when the internal temperature is higher than the set value is that it is necessary to lower the surface temperature and thereby to effect auxiliary temperature adjustment also at the body surface so that the internal temperature quickly returns to the set value. For this reason, the coaxial switch 18 is maintained at the dummy load side thereafter, so that no heating is carried out (Step 160 in FIG. 9).

Since the second embodiment operates in this manner, the heating characteristic curve thereof is similar to that of the first embodiment (see FIG. 6).

Thus, it is possible according to the second embodiment to obtain advantageous effects which are substantially the same as those which are offered by the first embodiment. In addition, it is advantageously possible for the control of heating the cancerous cells within the body to be even more smoothly and precisely effected by auxiliarily controlling the surface temperature of the body.

Third Embodiment

A third embodiment of the invention will be described hereinunder with reference to FIGS. 8, 10 and 11.

This embodiment aims at effecting the control of the surface temperature even more accurately in addition to accomplishment of an object which is similar to that of the above-described second embodiment.

Figure 10:
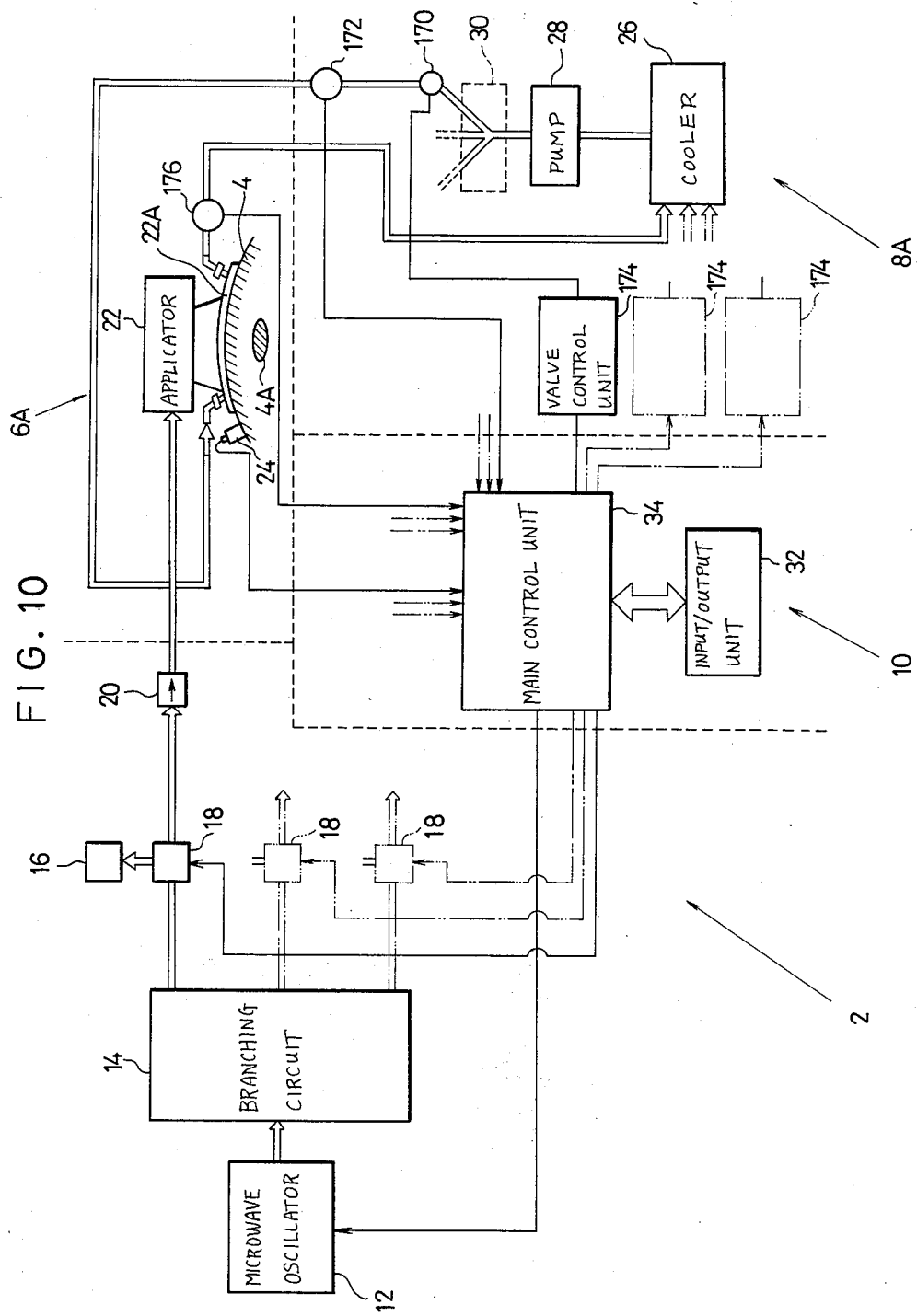
FIG. 10 is a general system diagram of a third embodiment of the invention.

To this end, a coolant temperature sensor 176 serving as one of the heated region temperature detecting means is additionally provided on the outlet side of the cooling mechanism 22A of each applicator 22 in the electromagnetic wave irradiating section 6A (see FIG. 10). The coolant temperature information obtained by each of the coolant temperature sensors 176 is input to the main control unit 34 with respect to each treatment system by the switchover operation of the multiplexer 20 in a manner similar to that in each of the above-described embodiments, and is employed as a reference value for various controls. The reason why the coolant temperature information is incorporated in the operation of controlling the surface temperature is that the temperature of cooling water is substantially equal to the surface temperature of the body of a patient in a stationary state and it is therefore possible for the surface temperature to be indirectly obtained from the degree of change in the temperature of the cooling water on the outlet side of each cooling mechanism 22A.

The arrangement of the other portions of this embodiment is the same as that of the second embodiment.

The operation of the third embodiment will now be described. In this case, it is assumed that a target value for the internal temperature is set at 43° C., while a target value for the surface temperature is set at 20° C.

Figure 11:
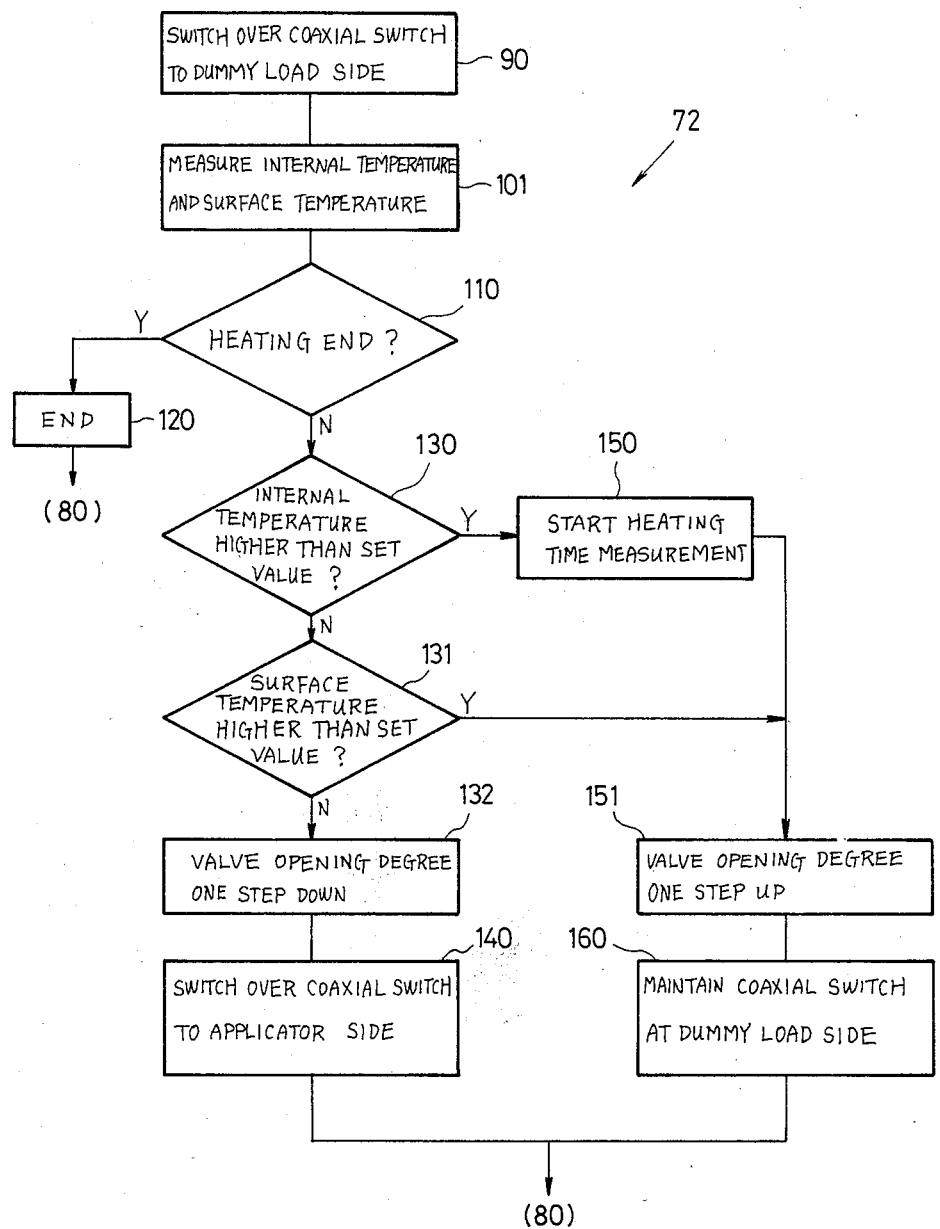
FIG. 11 is a flow chart which shows the operation of the flow chart of FIG. 8.

First, initial setting is effected in a manner similar to that in the control shown in FIG. 8 which illustrates the operation of the second embodiment. Thereafter, the control which is shown in FIG. 11 is effected for each of the patients by time-division multiplexing. In the controlling shown in FIG. 11, the following two steps are added to those of the second embodiment (see FIG. 9), and the other control operations are effected in a manner similar to that in the control shown in FIG. 9;

(1) The measurement of the surface temperature of the body of each patient is effected on the basis of the coolant temperature information delivered from the corresponding coolant temperature sensor 176 in addition to the internal temperature (Step 101 in FIG. 11).

(2) The control in this embodiment incorporates a judgement as to whether or not the surface temperature is higher than the set value (Step 131 in FIG. 11), and after this judgement, the valve control and the microwave irradiation control are carried out.

Accordingly, this embodiment has a heating characteristic curve which is similar to that shown in FIG. 6. It is therefore possible to obtain advantageous effects which are equivalent to those offered by the second embodiment. Since in this embodiment the surface temperature, in addition to the internal temperature, is employed as a reference value for effecting a feedback control, it is possible for the surface temperature to be more accurately and stably maintained at a predetermined value (e.g., 20° C.) at which the patient suffers no pain. Thus, it is advantageously possible to prevent the occurrence of any thermal burn or the like which would otherwise be caused by a rise in temperature as the result, for example, of a sudden change in the blood flow.

It is to be noted that, in the third embodiment, if the cancerous cells 4A exist on the body surface or in its vicinity (in the case of skin cancer, for example), it is also possible to effect hyperthermia treatment in a manner similar to the above by employing an arrangement wherein the internal temperature sensors 24 are removed and the coolant temperature sensors 176 are used alone. In such a case, since the treatment is carried out in a non-invasion manner wherein no temperature sensor is stuck into the body of the patient, it is conveniently unnecessary to take into consideration possible measuring errors which may be caused by microwaves during the temperature measurement period. It is therefore possible to omit the Step 90 (see, e.g., FIG. 11).

Fourth Embodiment

A fourth embodiment of the invention will now be described with reference to FIGS. 12 to 14.

This embodiment aims at accomplishing an object which is similar to that of the second embodiment. To this end, according to this embodiment, the temperature of cooling water itself is controlled.

Figure 12:
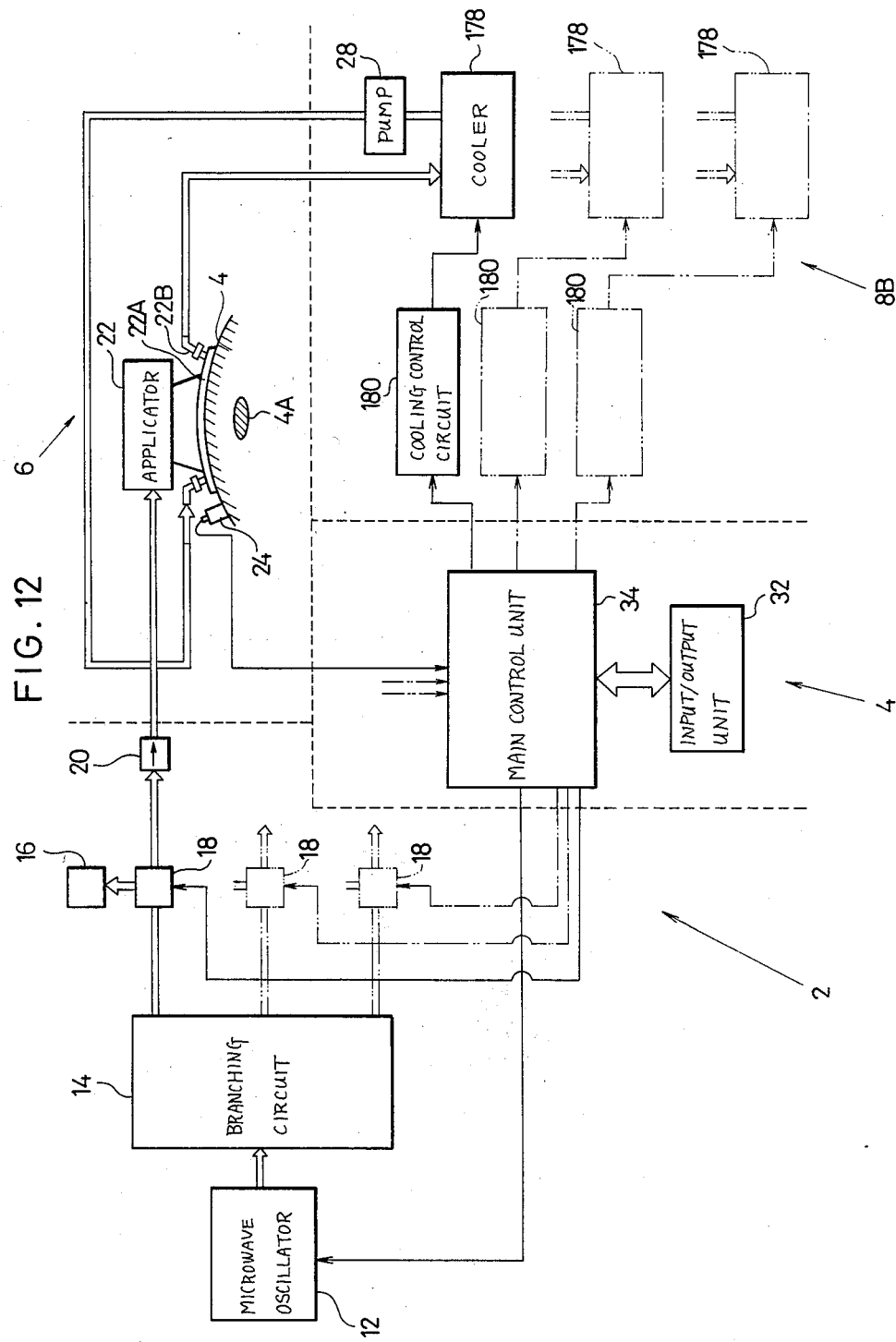
FIG. 12 is a general system diagram of a fourth embodiment of the invention.

Referring first to FIG. 12, the coolant supply section 8B of the fourth embodiment is provided with coolers 178 each of which cools the coolant for the corresponding one of three patients, and cooling control circuits 180 each controlling the corresponding cooler 178 such as to adjust the temperature of the coolant, thus constituting a cooling system for each patient. Accordingly, in this case, information about the internal temperature of each body 4 is delivered to the main control unit 34 from the corresponding internal temperature sensor 24 which serves as one of the heated region temperature detecting means. The main control unit 34 comprehensively makes a decision on the basis of the thus delivered temperature information and instruction information input by the operator when controlling the switching operation of each of the coaxial switches 18, and delivers a control signal to each of the cooling control circuits 180. In response to this control signal, each cooling control circuit 180 controls the corresponding cooler 178, thereby properly varying the temperature of the cooling water.

The arrangement of the other portions of this embodiment is the same as that of the second embodiment.

The general operation of the fourth embodiment will now be explained with reference to FIGS. 13 and 14. In this case, it is assumed that a target value for the internal temperature is set at 43° C.

Figure 13:
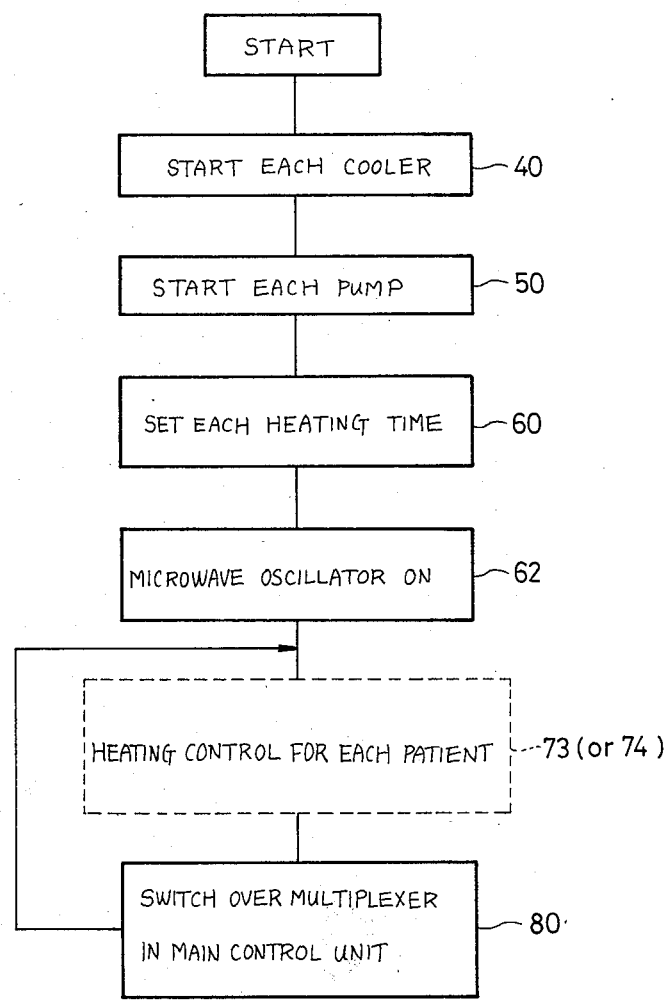
FIG. 13 is a flow chart which shows the operation of the embodiments respectively illustrated in FIGS. 12 and 15.

First, each cooler 178 is started (Step 40 in FIG. 13), and each pump 28 is started (Step 50 in FIG. 13). Then, a heating time for each of the patients is set (Step 60 in FIG. 13), and the microwave oscillator 12 is turned ON (Step 62 in FIG. 13). Thereafter, the heating control for each patient is effected (Steps 73 and 80 in FIG. 13) by time-division multiplexing in a manner similar to that in the second embodiment (see FIG. 5).

Figure 14:
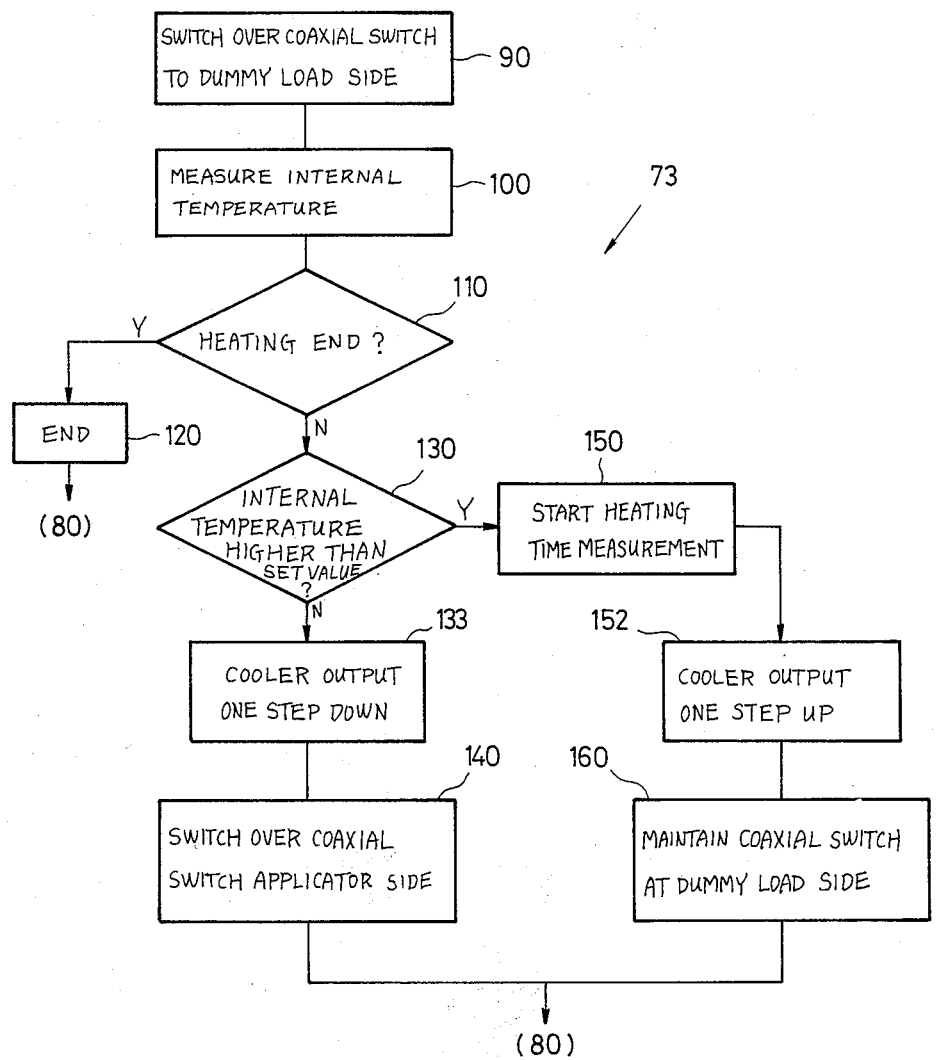
FIG. 14 is a flow chart which shows the operation of the embodiment illustrated in FIG. 12.

FIG. 14 shows in detail a flow chart for the control which is effected for each patient and which is shown in Step 73 in FIG. 13. According to the flow chart shown in FIG. 14, after a judgement (Step 130 in FIG. 14) has been made as to whether or not the internal temperature is higher than the set value, a cooling control is effected in such a manner that the output (cooling capacity) of the cooler 178 is stepped down (Step 133 in FIG. 14) or up (Step 152 in FIG. 14) by one degree. The other control operations of this embodiment are the same as those shown in FIG. 9 which illustrates the operation of the second embodiment. The reason why the cooling capacity is stepped down or up by one degree in the above-described control is the same as that in the case of the second embodiment in which the valve 170 is closed or opened by one degree. Accordingly, this embodiment also has a heating characteristic curve which is similar to that shown in FIG. 6.

Thus, it is possible to obtain advantageous effects which are substantially equivalent to those which are offered by the second embodiment. In addition, since it is relatively easy in the fourth embodiment to control the coolant temperature itself and since the coolant paths are independently arranged for individual patients, there is no interference between the coolant paths, which fact advantageously stabilizes the cooling control.

Fifth Embodiment

Figure 15:
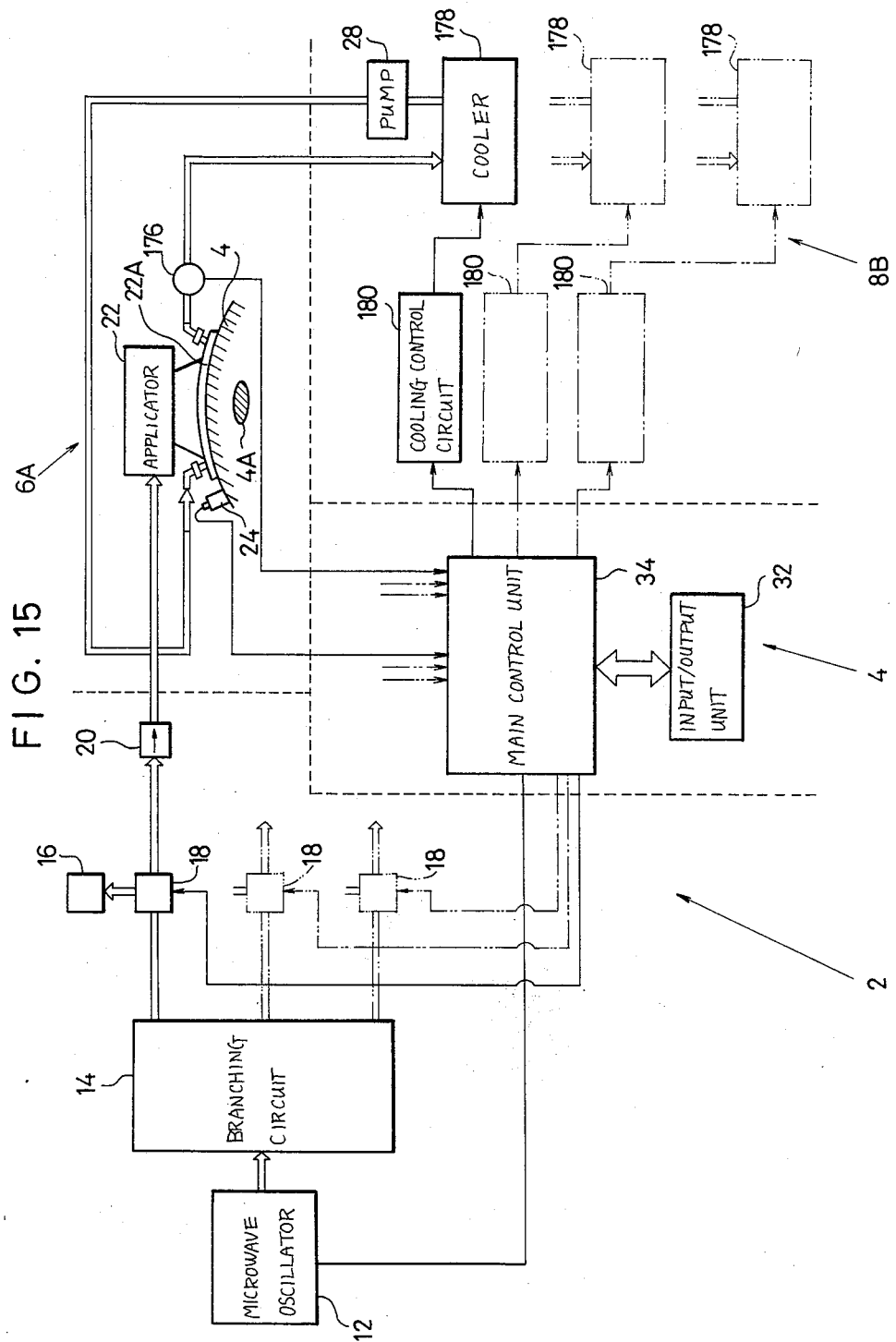
FIG. 15 is a general system diagram of a fifth embodiment of the invention.

A fifth embodiment of the invention will be described hereinunder with reference to FIGS. 13, 15 and 16.

This embodiment aims at accomplishing an object which is similar to that of the third embodiment.

To this end, the arrangement of the electromagnetic wave irradiating section 6A of the fifth embodiment is the same as that of the third embodiment. More specifically, the coolant temperature sensors 176 each serving as one of the heated region temperature detecting means are, as shown in FIG. 15, provided in addition to those constituent elements which are provided in the fourth embodiment.

The arrangement of the other portions and the function of each section of the fifth embodiment are the same as those in the third and fourth embodiments.

The following is a description of the general operation of the fifth embodiment. In this case, it is assumed that a target value for the internal temperature is set at 43° C., while a target value for the surface temperature is set at 20° C.

Figure 16:
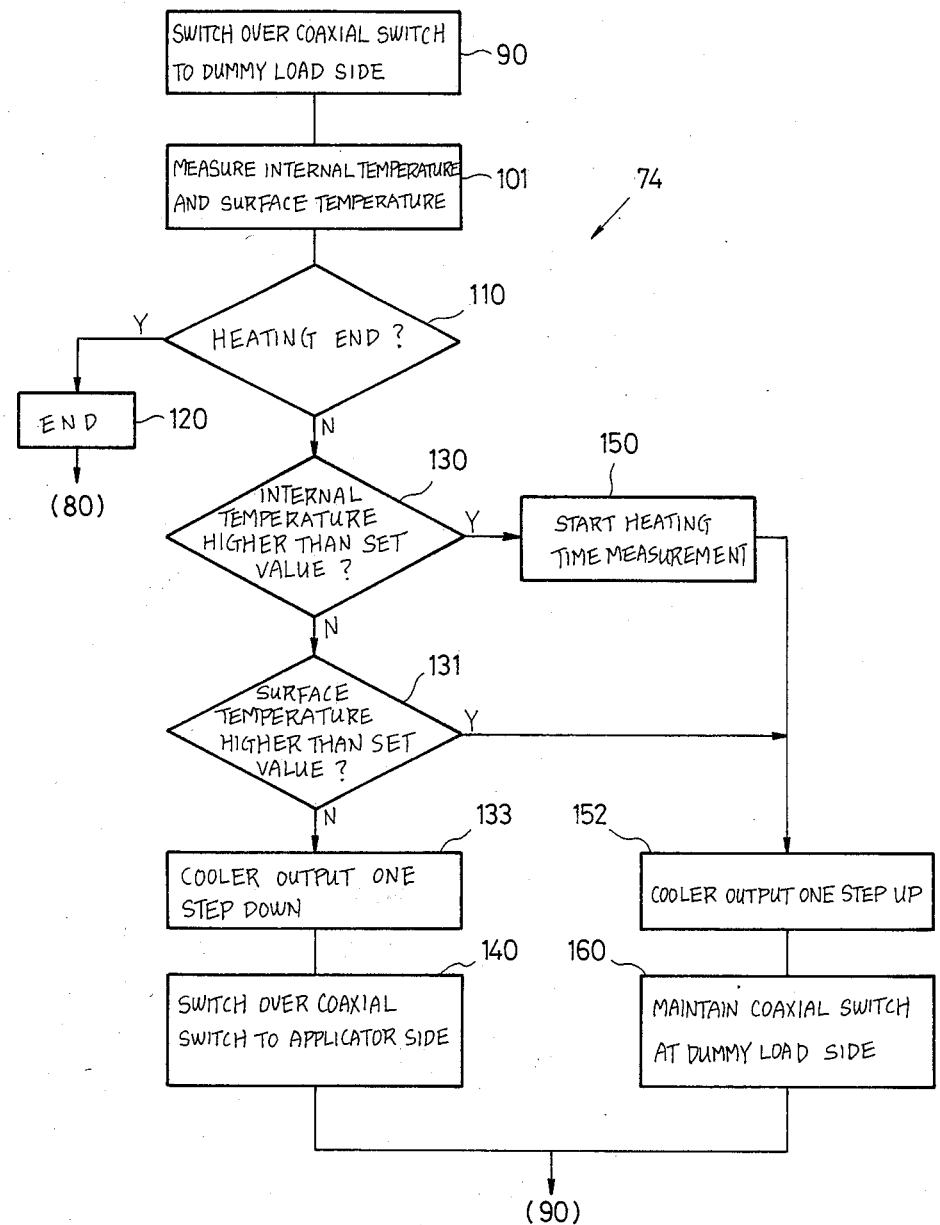
FIG. 16 is a flow chart which shows the operation of the embodiment illustrated in FIG. 15, in cooperation with the flow chart of FIG. 13.

First, the initial setting is effected in a manner similar to that shown in FIG. 13 which illustrates the operation of the fourth embodiment. Thereafter, the control shown in FIG. 16 is effected for each of the patients by time-division multiplexing. In the control shown in FIG. 16, the following two steps are added to those in the fourth embodiment (see FIG. 14), the other control operations being similar to those shown in FIG. 14:

(1) The surface temperature of the body of each patient is measured on the basis of not only the internal temperature but also the coolant temperature information delivered from the corresponding coolant temperature sensor 176 (Step 101 in FIG. 16).

(2) The control in this embodiment incorporates a judgement (Step 131 in FIG. 16) as to whether or not the surface temperature is higher than the set value, and after this judgement, the valve control and microwave irradiation control are effected.

Accordingly, this embodiment has a heating characteristic curve which is similar to that shown in FIG. 6. In consequence, it is possible according to the fifth embodiment to obtain advantageous effects which are equivalent to those offered by the third embodiment. Since the coolant paths are independently arranged for the individual patients for the purpose of effecting the coolant temperature control, there is not interference between the coolant paths, which fact advantageously enables a stable cooling control to be obtained.

It is to be noted that it is possible in the fifth embodiment to eliminate the internal temperature sensors 24 and effect a non-invasion hyperthermia treatment in a manner similar to the above in such a case as skin cancer where cancerous cells 4A exist on the body surface or in the vicinity thereof.

In the second or fifth embodiment, when the hyperthermia treatment being carried out is so arranged that the number of patients who are to be subjected to hyperthermia treatment is always equal to the number of branched outputs of the branching circuit 14 serving as an electromagnetic wave branching means, it is possible for the object of the embodiment to be accomplished satisfactorily even if the coaxial switches 18 serving as electromagnetic wave switching means and the dummy loads 16 are omitted. In such a case, it becomes unnecessary to specially provide the internal temperature sensors 24 when, for example, sequence control is effected in accordance with a hyperthermia program which has previously been prepared for each of the patients. In consequence, it is possible for the arrangement of the system to be further simplified.

Sixth Embodiment

A sixth embodiment of the invention will now be described with reference to FIGS. 17 to 23.

This embodiment aims at providing a more effective hyperthermia treatment for each of the patients at the same time and in parallel with each other by adding another function to the electromagnetic wave supply section 2 in the first embodiment, such function enabling the microwave output level to be adjusted for each patient.

Figure 17:
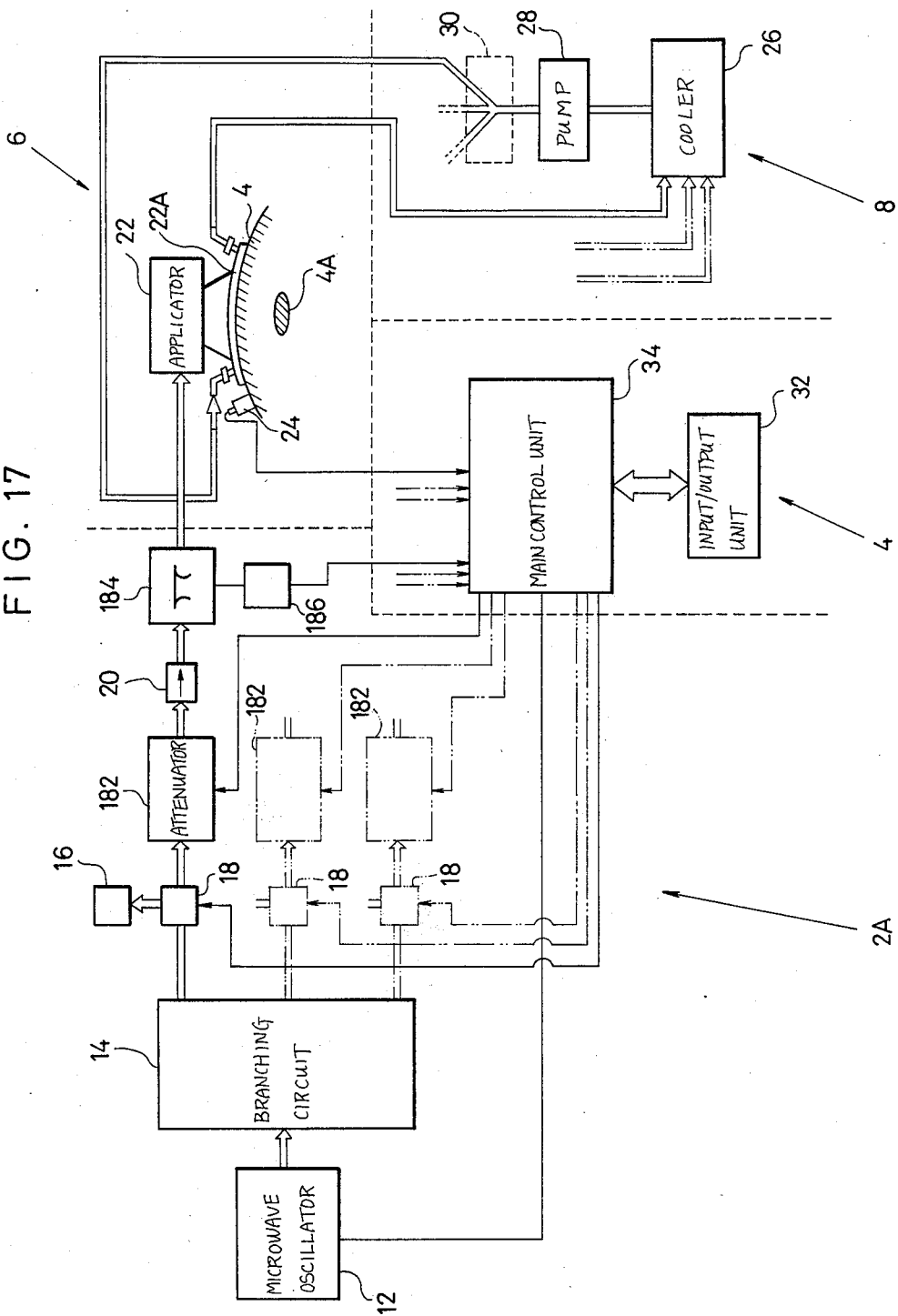
FIG. 17 is a general system diagram of a sixth embodiment of the invention.

To this end, the electromagnetic wave supply section 2A of the sixth embodiment is, as shown in FIG. 17, additionally provided with attenuators 182 which are respectively disposed between the coaxial switches 18 and the isolators 20, each of the attenuators 182 serving as an electromagnetic wave attenuating means which automatically adjusts the microwave output level in accordance with the instructions delivered from the main control unit 34. Further, directional couplers 184 are respectively provided between the isolators 20 and the applicators 22. Each of the directional couplers 184 has its subsidiary waveguide side leading to the main control unit 34 in the control section 4 through a detector circuit 186.

Accordingly, incident and reflected waves are taken out from each directional coupler 184 while being isolated from each other, and each of the isolated waves is detected and converted into a voltage by the corresponding detector circuit 186 before being delivered to the main control unit 34. The main control unit 34 obtains, for example, a reflection coefficient for each microwave path and calculates a microwave power which is effectively supplied to the corresponding applicator 22. The result of this calculation is employed for automatic adjustment of the attenuation rate of microwaves, that is, the microwave output level.

The arrangement of the other portions of this embodiment is the same as that of the first embodiment.

Accordingly, the main control unit 34 receives information detected by the directional couplers 184 and the internal temperature sensors 24 respectively provided for three patients through the multiplexer and the A/D (analog-digital) converter (both are not shown). On the basis of the detected information thus received and the operator instruction information obtained through the input/output section 32, the main control unit 34 effects predetermined controls and judgements and delivers predetermined control signals through the D/A (digital-to-analog) converter (not shown) and the multiplexer (not shown) which is sequentially switched over. In response to the control signals, the attenuation rate of each of the attenuators 182 and the switching operation of each of the coaxial switches 18 are automatically controlled, and the internal temperature of each of the patients is thereby advantageously maintained at the set value, or values in the approximate vicinity of it, at all times.

Figure 18:
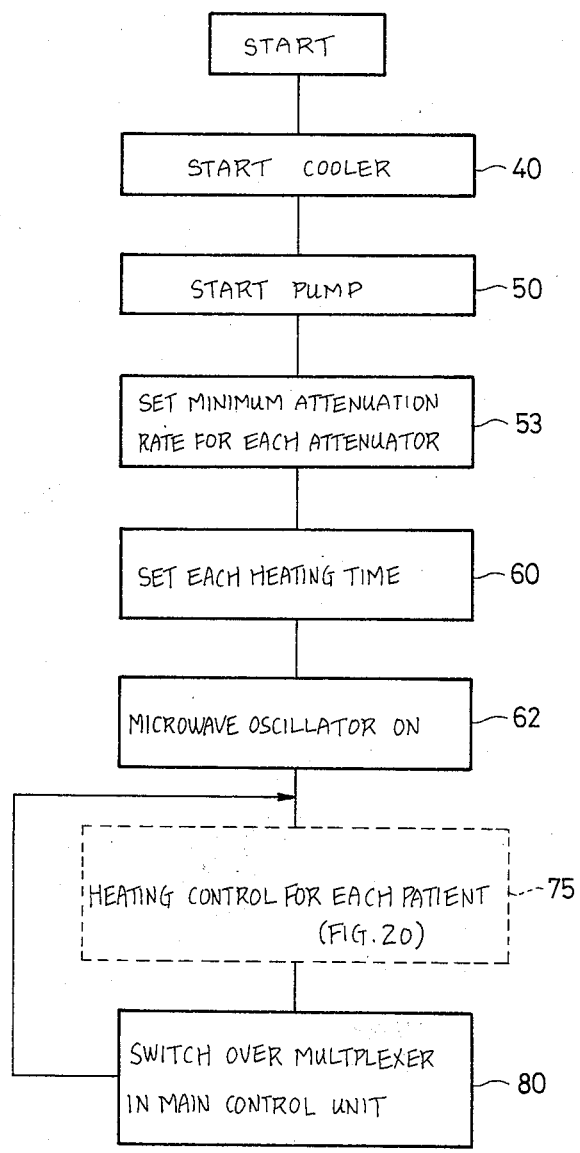
FIGS. 18 and 19 are flow charts which show the operation of the embodiment shown in FIG. 17.

The following is a description of the general operation of the sixth embodiment with reference to FIG. 18. In this case, it is assumed that a target value for the internal temperature is set at 43.5° C.

First, in a manner similar to that in each of the above-described embodiments, the cooler 26 is started (Step 40 in FIG. 18), and the pump 28 is started (Step 50 in FIG. 18). Then, the main control unit 34 sets a minimum attenuation rate (that is, a maximum output value for microwaves) for each of the attenuator 182 (Step 53 in FIG. 18). This setting is effected by combining a value for the microwave output which is effectively supplied to each applicator 22 and which is obtained on the basis of the detected information delivered from the corresponding directional coupler 184 with a value (depth) which is set by the operator through the input/output unit 32 in accordance with the depth below the skin of the cancerous cells within the body of the patient concerned. It is assumed in this embodiment that maximum outputs of microwaves for the three patients which are set in Step 53 in FIG. 18 are respectively represented by $P_1$, $P_2$ and $P_3$. It is to be noted that the above-described minimum attenuation rates may be previously set by employing a phantom model.

Figure 20:
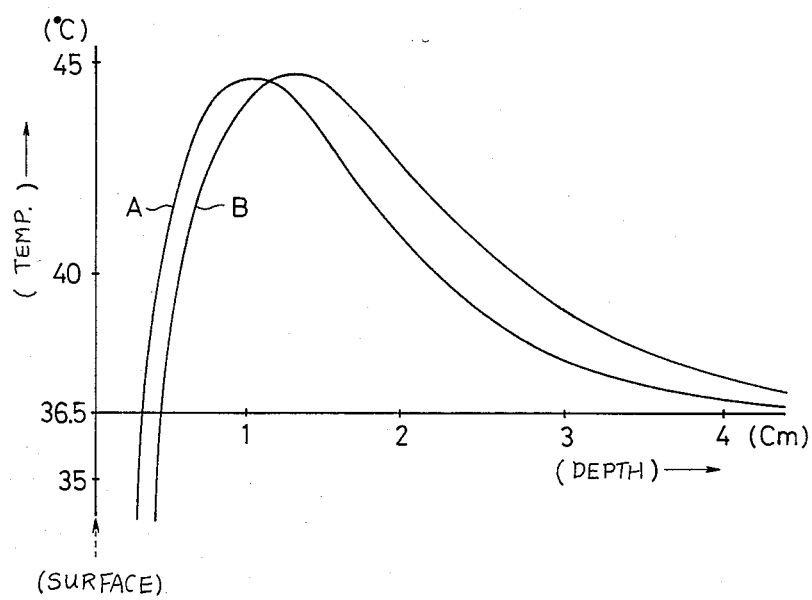
FIGS. 20 and 21 are graphs which show temperature distribution with respect to depth below the skin of a living body.
Figure 21:
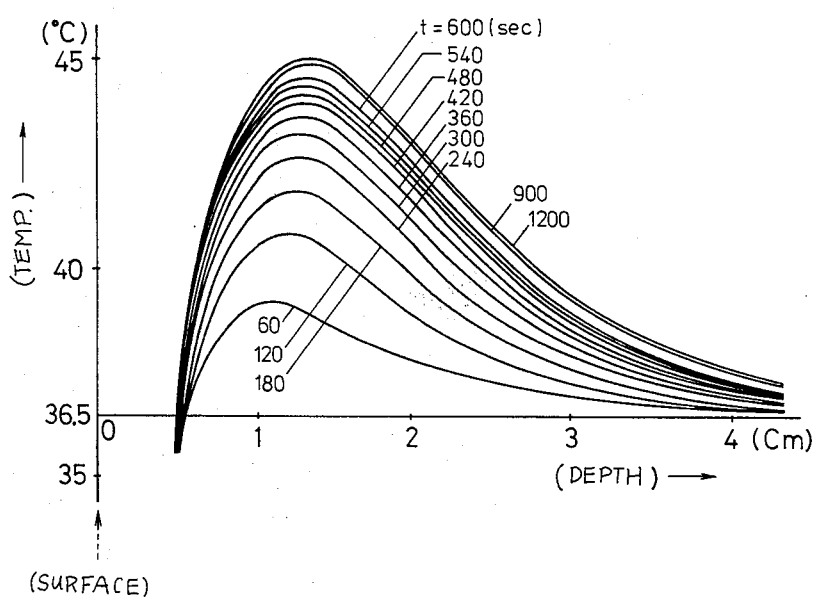

Incidentally, the reason why a minimum attenuation rate for each of the attenuators 182 is set in accordance with the depth of the cancerous cells as described above is as follows. Namely, as the microwave output is increased (that is, the attenuation rate is decreased) the temperature peak in heating is shifted toward the surface of a body, whereas as the microwave output is decreased (that is, the attenuation rate is increased) the temperature peak is shifted toward the inside of the body since in such a case the heat gradually penetrates into the body. FIG. 20 is a graph which represents the results of experiments carried out on a phantom model which approximated to a living body. The graph shows comparison between a temperature distribution (A) obtained by irradiating the phantom model with a microwave of 2,450MHz on the basis of a reference quantity, and a temperature distribution (B) obtained by irradiating the phantom model with a microwave whose output was set by subtracting 3 dB from that reference quantity. Such a frequency band is highest in the frequency regions for hyperthermia and consequently the range of temperature peaks is limited to the surface layer of the phantom model. It may nevertheless be understood that the temperature distribution (B) has a temperature peak at a portion which is about 0.25 cm deeper than that of the temperature distribution (A). However, a reduction in the microwave output requires a corresponding increase in the time taken to heat cancerous cells up to a target temperature. FIG. 21 is a graph which shows changes in temperature of a heated region measured for each predetermined period of time. The curves in the graph represent heating characteristics in this embodiment.

After a minimum attenuation rate for each attenuator 182 has thus been set, the operator sets a heating time which is matched with the particular condition of each of the patients (Step 60 in FIG. 18). Then, the microwave oscillator 12 is turned ON (Step 62 in FIG. 18).

After these initial values have been set as described above, the heating control shown in FIG. 19 is effected for each of the patients (Steps 75 and 80 in FIG. 18) by time-division multiplexing (see FIG. 5).

Figure 19:
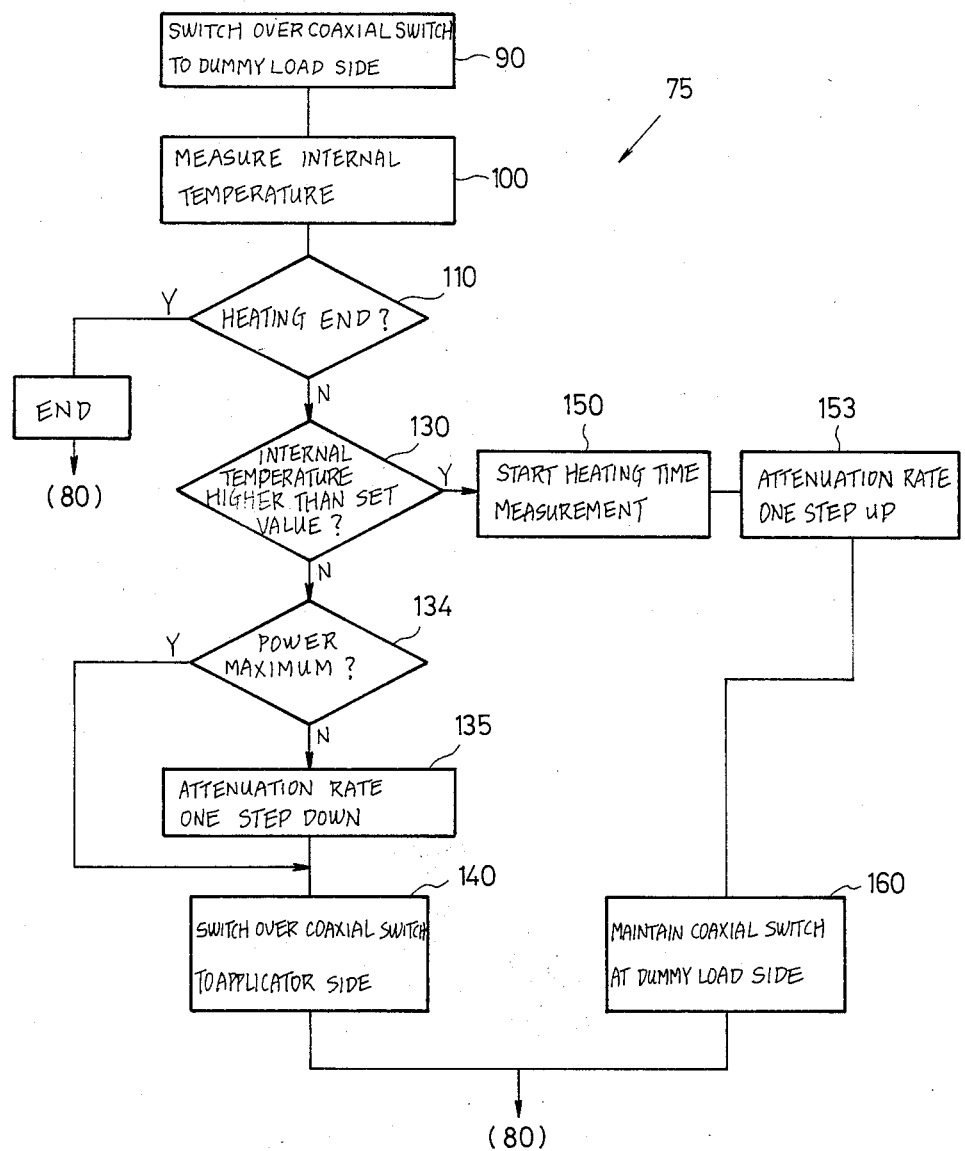

According to the heating control shown in FIG. 19, the operation of this embodiment is similar to that of the first embodiment which is shown in FIG. 4, except for the following two additional functions:

(1) When the internal temperature is lower than the set value, the main control unit 34 steps down the attenuation rate for the corresponding attenuator 182 by one degree, thereby increasing the output setting value for the electromagnetic energy which is to be supplied to the body of the patient concerned. However, in this case it is necessary for the attenuation rate thus stepped down to be above the initially set minimum attenuation rate (Steps 134 and 135 in FIG. 19). Then, the corresponding coaxial switch 18 is switched over to the applicator side, whereby microwave irradiation is effected on the basis of the newly set value (Step 140 in FIG. 19), and heating is continued until a subsequent clock pulse occurs. This heating and the measurement of internal temperature (Step 100 in FIG. 19) are repeated until the internal temperature exceeds the set value, and the attenuation rate for the attenuator 182 is stepped down by one degree every time this control process is executed (Steps 134 and 135 in FIG. 19).

(2) On the other hand, when the internal temperature becomes higher than the set value, measurement of the heating time is started (Step 150 in FIG. 19) (However, this Step is executed only in the first control operation), and the attenuation rate for the attenuator 182 is stepped up by one degree (Step 153 in FIG. 19). At this time, the coaxial switch 18 is maintained at the dummy load side (Step 160 in FIG. 19), whereby the heating is suspended.

Thus, since the microwave output in this embodiment is finely controlled, it is possible to carry out a precise hyperthermia treatment. Experimental examples of this embodiment are shown in FIGS. 22 and 23.

Figure 22:
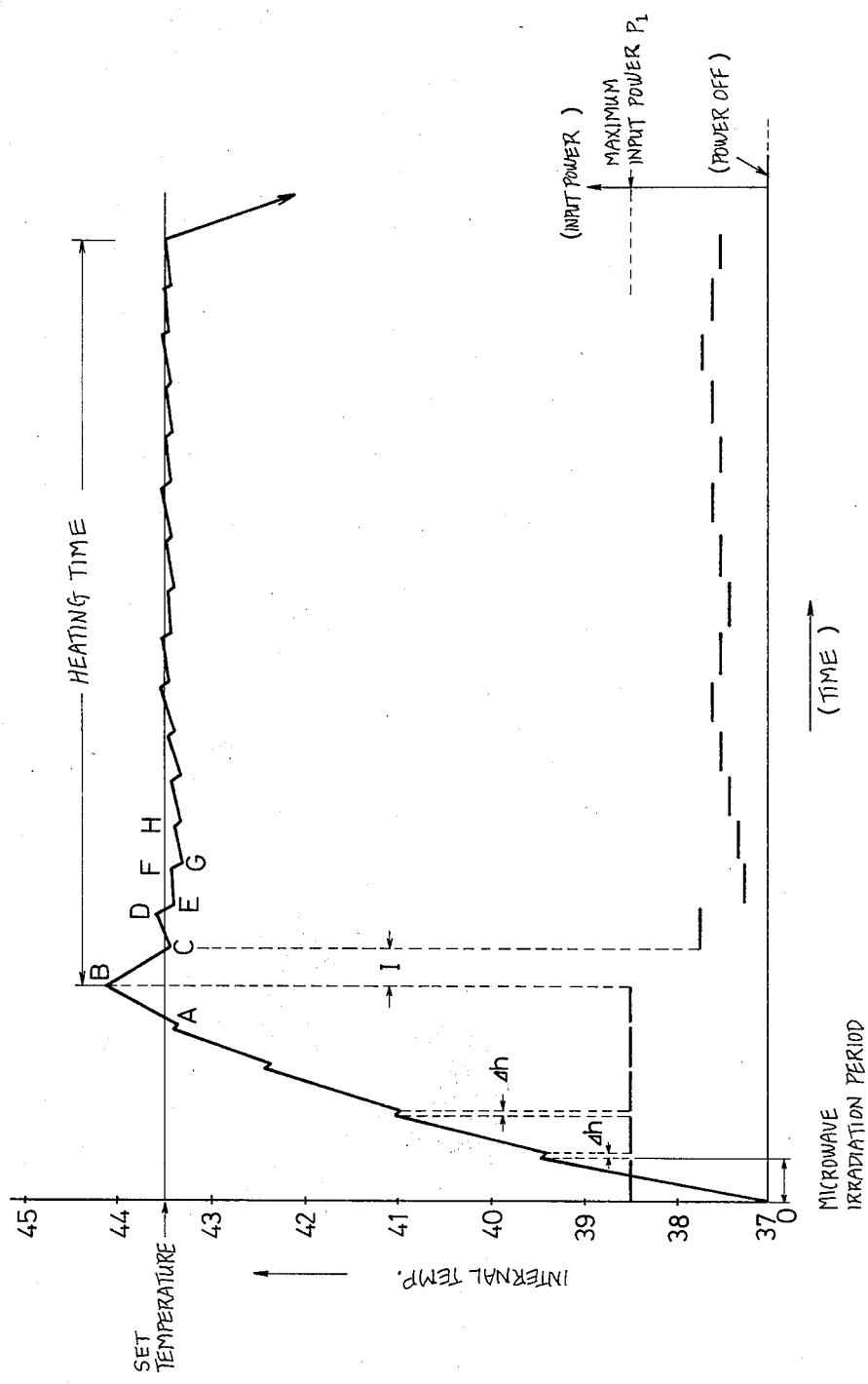
FIGS. 22 and 23 are graphs which show the action and operation of the embodiment illustrated in FIG. 17.
Figure 23:
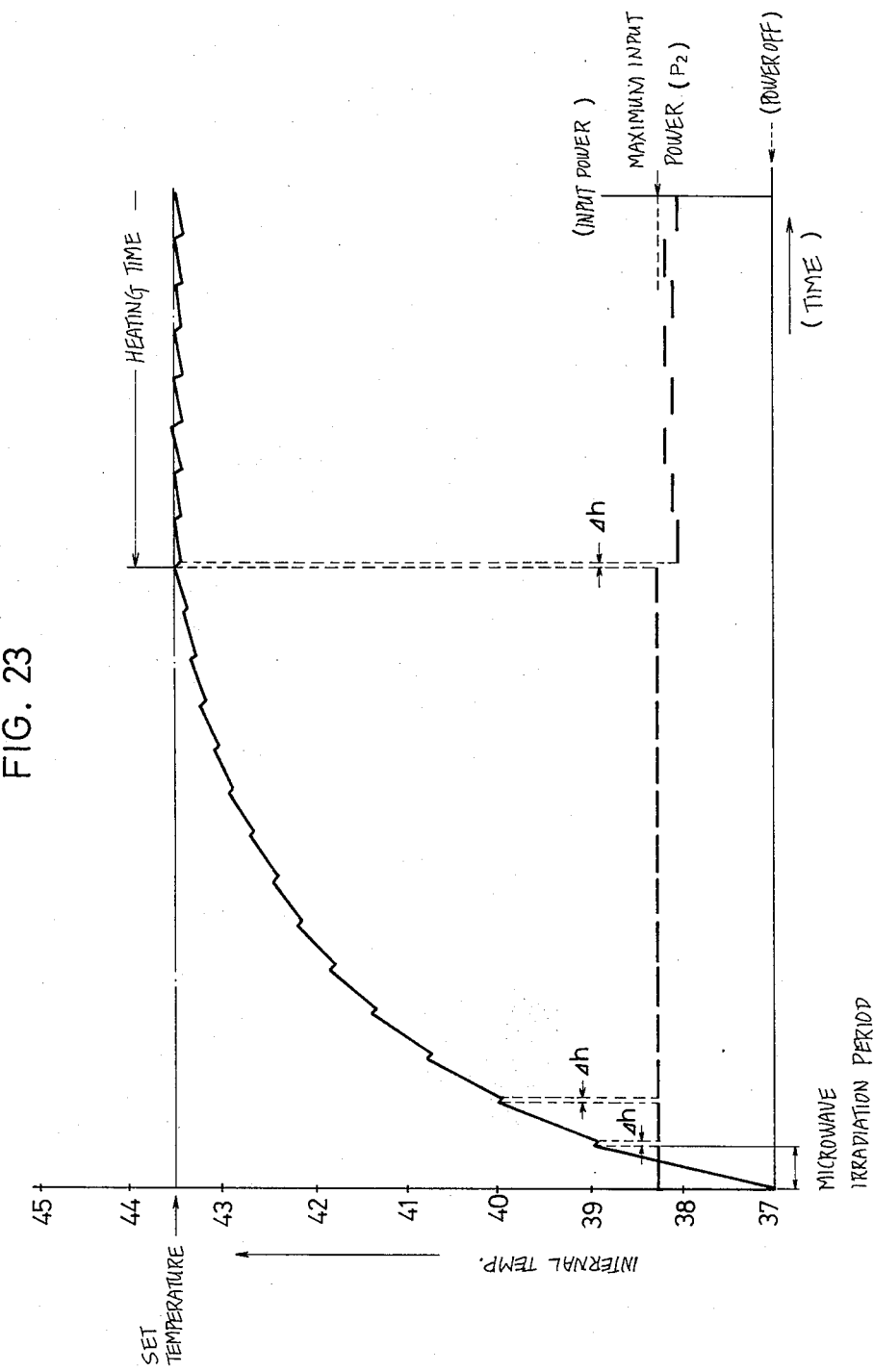

FIG. 22 shows changes with time in the internal temperature (the temperature of cancerous cells) of a single patient measured during each microwave irradiation period, each non-irradiation period and each internal temperature measuring period (during which an individual heating control shown in FIG. 19 is processed), together with changes in the microwave output.

In FIG. 22, each of the intervals in which the internal temperature curve ascends corresponds to a microwave irradiation period, while each of the intervals Δh in which the temperature curve descends corresponds to a period during which an internal temperature measuring operation is effected in synchronism with one clock pulse as shown in FIG. 5. During each of the internal temperature measuring periods, no microwave irradiation is effected, as pointed out above. The point B in FIG. 22 represents a point of time at which the internal temperature first exceeds the set value as the result of the microwave irradiation by a maximum output (P1)

on the basis of the minimum attenuation rate of the attenuator 182 and the measurement of the heating time is hence started. The above-described heating time is counted from this point B. Thereafter, instructions are continuously given to the effect that no microwave irradiation is to be performed during each internal temperature measuring period until the internal temperature reaches 43.5° C. or below (see Step 160 in FIG. 19). During this period (the period between B and C in FIG. 22), the microwave output which is to be subsequently applied is newly set, and at the point of time when the internal temperature reaches 43.5° C. or below, microwave irradiation is resumed (during the period between C and D in FIG. 22). The time I between B and C corresponds to the time I, for example, which is shown in FIG. 5. During the period between C and D in FIG. 22, the internal temperature curve is less in terms of the degree of slope than that between A and B since the microwave output setting value has been lowered.

In the case where the internal temperature does not reach 43.5° C. in the next microwave irradiation (e.g., during the period between E and F in FIG. 22) since the microwave output setting value has been excessively lowered during an internal temperature measuring period, the microwave output is stepped up during the next internal temperature measuring period (e.g., the period between F and G in FIG. 22) as shown in Step 135 in the flow chart of FIG. 19. In consequence, the degree of slope of the internal temperature curve is increased again (e.g., the period between G and H in FIG. 22). By virtue of such repetition of control, it is possible to obtain an internal temperature control which involves substantially no ripple in heating for each of the patients.

On the other hand, FIG. 23 shows changes in the internal temperature with time in the case where a minimum attenuation rate for the attenuator 182 is set at a relatively high value, that is, the maximum microwave output is set at a relatively low value ($P_2$) since the targeted cancerous cells are present in a relatively deep part of the body of the patient. With respect to a patient who has a cancerous condition of this sort, hyperthermia treatment is effected in synchronism with, for example, a clock pulse 2 shown in FIG. 5. Thus, it is advantageously possible for various patients to be individually subjected to treatments which are individually suitable to them at the same time and in parallel with each other, even when the conditions of these patients differ from one another.

As described above, it is possible according to the sixth embodiment to obtain advantageous effects which are substantially equivalent to those offered by the first embodiment. In addition, it is possible for the level of microwave output which is applied to the body to be finely adjusted for each patient. It is therefore advantageously possible for a plurality of patients to be subjected to a more precise hyperthermia treatment at the same time and in parallel with each other.

It is to be noted that, although in the sixth embodiment each attenuator 182 serving as an electromagnetic wave attenuating means is automatically adjusted by means of the main control unit 34, the arrangement may be such that the attenuation rate for each attenuator 182 is manually set by the operator in accordance with need (in such a case, no directional coupler 184 is required). In this case, it is favorably possible to simplify the arrangement of the system.

Figure 24:
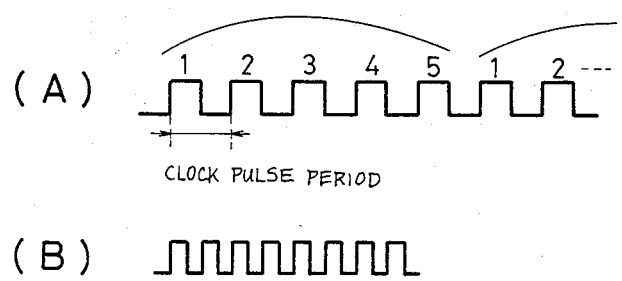
FIGS. 24(A) and 24(B) are timing charts which respectively show other examples of a synchronizing clock pulse train.

It is to be noted also that, although the number of patients who are subjected to hyperthermia treatment is three in each of the above-described embodiments, the number of patients may be increased. In such a case (e.g., where the number of patients is five), it is only necessary to change the clock pulse train shown in FIG. 5 into one such as that shown in FIG. 24(A). By controlling or varying the period of this clock pulse train, it is possible to determine a microwave irradiation period which is defined between two adjacent internal temperature measuring periods. Accordingly, if the period of the clock pulse train is reduced in such a manner as that shown in FIG. 14(B), the microwave irradiation interval is reduced correspondingly. It is therefore possible for an increased number of patients to be simultaneously subjected to hyperthermia treatment. Even in such a case, no problem is experienced with the treatment since the internal temperature measuring period ($\Delta h$) is also extremely short and therefore ignorable for practical purposes. When the number of patients is increased, it is only necessary to correspondingly increase the number of branched output terminals of the branching circuit 14. Additionally, in place of the isolators 20 shown in FIG. 1 the general system diagrams, combinations of circulators and dummy loads may be employed to prevent any reflected waves from undesirably entering the branching circuit 14. Further, the microwave oscillator 12 may be controlled by employing an inverter.

What is claimed is:
1. Hyperthermia apparatus comprising:
   (a) at least one treatment branch including:
      (1) a microwave source for generating microwaves that are applied to the branch;
      (2) an applicator for applying microwaves in the branch to a treatment region of a patient;
      (3) a cooling mechanism for cooling the surface of said treatment region when coolant is supplied to said cooling mechanism;
      (4) a coolant reservoir;
      (5) adjustable means connecting said reservoir to said cooling mechanism for supplying coolant to said mechanism in step-wise variable amounts; and
   (b) a main control unit comprising:
      (1) means for periodically reducing the power level in said branch to zero;
      (2) means made effective each time the power level in said branch is zero for measuring internal and surface temperatures of said treatment region; and
      (3) means responsive to the internal and surface temperatures each time they are measured for adjusting said adjustable means such that coolant flow is controlled in accordance with the measured internal and surface temperatures.

2. Hyperthermia apparatus according to claim 1 wherein said means responsive to the internal and surface temperature is constructed and arranged such that the coolant flow is increased by one step is either the measured internal temperature exceeds a preset internal temperature value, or the measured surface temperature exceeds a preset surface temperature value.

3. Hyperthermia apparatus according to claim 2 wherein said means responsive to the internal and surface temperature is effective to adjust said adjustable means such that coolant flow is decreased by one step if the surface temperature is less than said preset surface temperature value.

4. Hyperthermia apparatus according to claim 3 including a plurality of treatment branches like that set forth in subparagraph (a) in claim 1, wherein said main control unit independently controls the power level and cooling in each branch.

5. Hyperthermia apparatus according to claim 1 wherein said means responsive to the internal and surface temperatures is effective to adjust said adjustable means such that coolant flow is decreased by one step if the surface temperature is lower than a preset surface temperature value, or is increased by one step if the surface temperature is higher said preset surface value.

6. Hyperthermia apparatus according to claim 1 wherein the treatment branch includes a cooler for extracting heat from said coolant, a pump for exchanging coolant between said cooling mechanism and said cooler, and a selectively operable valve interposed between said pump and said cooling mechanism, said valve constituting said adjustable means.

7. Hyperthermia apparatus according to claim 1 wherein said at least one branch includes a dummy load, and means controllable by said main control unit for switching the output of said source into said dummy load for reducing the power level in the branch to zero.

8. A method for treating a region of a patient with microwaves in a treatment branch, said method comprising the steps of:
 (a) cooling the surface of the region;
 (b) inputting said microwaves into a dummy load for reducing the power level in the treatment branch to zero for a predetermined period of time;
 (c) measuring the surface and internal temperatures of said region while the power level is zero;
 (d) reducing surface cooling by one step if neither the internal nor surface temperatures of said region exceeds respective preset values;
 (e) inputting said microwaves into an applicator that directs the microwaves into the treatment region for a predetermined period of time thereby heating said region; and
 (f) repeating steps (a)-(e).

9. A method according to claim 8 including the step of beginning to time heating of said region when the measured internal temperature reaches a preset value.

10. A method according to claim 9 including the steps of increasing the cooling by one step if either the internal or surface temperature exceeds respective preset values, and then carrying out steps (a)-(e) of claim 8.

* * * * *